:

US008637232B2

(12) United States Patent
Lama

(10) Patent No.: US 8,637,232 B2
(45) Date of Patent: Jan. 28, 2014

(54) BIOMARKERS FOR LUNG DISEASE MONITORING

(75) Inventor: Vibha Lama, Ann Arbor, MI (US)

(73) Assignee: The Regents of The University of Michigan, Ann Arbor, MI (US)

(*) Notice: Subject to any disclaimer, the term of this patent is extended or adjusted under 35 U.S.C. 154(b) by 56 days.

(21) Appl. No.: 13/011,541

(22) Filed: Jan. 21, 2011

(65) Prior Publication Data

US 2011/0250589 A1    Oct. 13, 2011

Related U.S. Application Data

(60) Provisional application No. 61/297,142, filed on Jan. 21, 2010.

(51) Int. Cl.
    *C12N 1/02*    (2006.01)
    *C12N 1/06*    (2006.01)
    *G01N 33/53*    (2006.01)

(52) U.S. Cl.
    USPC .......... 435/4; 435/29; 435/30; 435/34; 435/39

(58) Field of Classification Search
    None
    See application file for complete search history.

(56) References Cited

PUBLICATIONS

Lama et al. The Journal of Clinical Investigation http://www.jci.org vol. 117 No. 4 Apr. 2007, pp. 989-996.*
Mishra et al., 2008, "Carcinoma-associated fibroblast-like differentiation of human mesenchymal stem cells", Cancer Res. 68:4331-4339.
Miyahara et al., 2006, "Monolayered mesenchymal stem cells repair scarred myocardium after myocardial infarction", Nat Med. 12:459-465.
Needleman and Wunsch, 1970, "A general method applicable to the search for similarities in the amino acid sequence of two proteins," J Mol Biol, 48, pp. 443-453.
Nemeth et al., 2009, "Bone marrow stromal cells attenuate sepsis via prostaglandin E(2)-dependent reprogramming of host macrophages to increase their interleukin-10 production", Nat. Med. 15:42-49.
Noth et al., 2002, "Multilineage mesenchymal differentiation potential of human trabecular bone-derived cells," J Orthop Res, 20, pp. 1060-1069.
Ortiz et al., 2003, "Mesenchymal stem cell engraftment in lung is enhanced in response to bleomycin exposure and ameliorates its fibrotic effects," PNAS USA, 100, pp. 8407-8411.
Pearson and Lippman, 1988, "Improved tools for biological sequence comparison," Proc Natl Acad Sci USA, 85, pp. 2444-2448.
Peterson et al., 1997, "The winged helix transcriptional activator HFH-8 is expressed in the mesoderm of the primitive streak stage of mouse embryos and its cellular derivatives", Mech. Dev., 69:53-69.
Pierdomenico et al., 2005, "Multipotent mesenchymal stem cells with immunosuppressive activity can be easily isolated from dental pulp," Transplantation, 80, pp. 836-842.
Pierrou et al., 1994, "Cloning and characterization of seven human forkhead proteins: binding site specificity and DNA bending", EMBO J., 13:5002-12.
Pittenger et al., 1999, "Multilineage potential of adult human mesenchymal stem cells," Science, 284, pp. 143-147.
Ramirez et al., 2004, "Smad3 deficiency ameliorates experimental obliterative bronchiolitis in a heterotopic tracheal transplantation model", Am. J. Pathol., 165:1223-32.
Rasmusson, 2006, "Immune modulation by mesenchymal stem cells," Exp Cell Res, 312, pp. 2169-2179.
Riise et al., 1999, "Persistent high BAL fluid granulocyte activation marker levels as early indicators of bronchiolitis obliterans after lung transplant", Eur. J. Respir. J. 14:1123-1130.
Rojas et al., 2005, "Bone marrow-derived mesenchymal stem cells in repair of the injured lung", Am. J. Respir. Cell Mol. Biol. 33:145-152.
Sabatini et al., 2005, "Human bronchial fibroblasts exhibit a mesenchymal stem cell phenotype and multilineage differentiating potentialities," Lab Invest, 85, pp. 962-971.
Sajjan et al., 2004, "Responses of well-differentiated airway epithelial cell cultures from healthy donors and patients with cystic fibrosis to *Burkholderia cenocepacia* infection", Infect. Immun., 72:4188-4199.
Salazar et al., 2009, "Mesenchymal stem cells produce Wnt isoforms and TGF-beta1 that mediate proliferation and procollagen expression by lung fibroblasts", Am. J. Physiol. Lung Cell Mol. Physiol., 297:L1002-1011.
Sambrook et al., 1989, "Molecular Cloning: A Laboratory Manual," Cold Spring Harbor Press, NY.
Schneider et al., 2010, "Increased cytokine response of rhinovirus-infected airway epithelial cells in chronic obstructive pulmonary disease", J. Respir. Crit. Care Med., 182:332-340.
Smith and Waterman, 1981, "Comparison of Biosequences," Adv Appl Math, 2, pp. 482.
Studer et al., 2008, "CD28 down-regulation on CD4 T cells is a marker for graft dysfunction in lung transplant recipients", Am. J. Respir Crit. Care Med. 178:765-773.
Tiroke et al., 1999, "Bronchoalveolar lavage in lung transplantation. State of the art", Clin. Transplant 13:131-157.
Tuteja et al., 2007, "Forkhead transcription factors II", Cell 131:192.
Tuteja et al., 2007, "SnapShot: forkhead transcription factors I", Cell 130:1160.
Uccelli et al., 2007, "Mesenchymal stem cells: a new strategy for immunosuppression," Trends Immunol, 28, pp. 219-226.
Volpe et al., 1997, "Hoxb-5 expression in the developing mouse lung suggests a role in branching morphogenesis and epithelial cell fate", Histochem. Cell Biol., 108:495-504.

(Continued)

*Primary Examiner* — Janet Epps-Smith
(74) *Attorney, Agent, or Firm* — Tanya A. Arenson; Casimir Jones, S.C.

(57) ABSTRACT

The present invention pertains to the monitoring and treatment of lung transplant recipients. In particular, the invention pertains to the use of biomarkers to predict or detect post-lung transplantation complications (e.g., organ rejection, acute organ rejection, organ injury, bronchiolitis obliterans, bronchiolitis obliterans syndrome, organizing pneumonia), fibroproliferative repair responses, interstitial lung diseases (e.g., idiopathic pulmonary fibrosis and other fibrotic lung diseases), and other immune-mediated lung diseases (e.g., graft versus host disease, scleroderma).

3 Claims, 13 Drawing Sheets

(56) References Cited

PUBLICATIONS

Volpe et al., 2000, "Hoxb-5 control of early airway formation during branching morphogenesis in the developing mouse lung", Biochem. Biophys. Acta, 1475:337-345.

Volpe et al., 2003, "Expression of Hoxb-5 during human lung development and in congenital lung malformations", Birth Defects Res. A Clin. Mol. Teterol., 67:550-556.

Vos et al., 2009, "C-reactive protein in bronchoalveolar lavage fluid is associated with markers of airway inflammation after lung transplantation", Transplant Proceedings, 41(8): 3409-13.

Walker et al., 2011, "Resident tissue-specific mesenchymal progenitor cells contribute to fibrogenesis in human lung allografts", American Journal of Pathology, 178(6): 2461-69 (Abstract Only).

Wilkes et al. (2005), "Lung transplantation: opportunities for research and clinical advancement", Am. J. Respir. Crit. Care Med. 172:944-955.

Willis et al., 2005, "Induction of epithelial-mesenchymal transition in alveolar epithelial cells by transforming growth factor-beta1: potential role in idiopathic pulmonary fibrosis", Am J Pathol., 166:1321-1332.

Willis et al., 2007, "TGF-beta-induced EMT: mechanisms and implications for fibrotic lung disease", Am. J. Physiol. Lung Cell Mol. Physiol., 293:L525-534.

Wu et al., 2005, "Contribution of mesenchymal progenitor cells to tissue repair in rat cardiac allografts undergoing chronic rejection", J. Heart Lung Transplant, 24:2160-2169.

Ye et al., 2006, "Mesenchymal stem cell transplantation in a rabbit corneal alkali burn model: engraftment and involvement in wound healing", Eye 20:482-490.

Young et al., "Human reserve pluripotent mesenchymal stem cells are present in the connective tissues of skeletal muscle and dermis derived from fetal, adult, and geriatric donors," Anat Rec, 264, pp. 51-62 (2001).

Yousem et al., 1996, "Revision of the 1990 working formulation for the classification of pulmonary allograft rejection: Lung Rejection Study Group", J. Heart Lung Transpl. 15(1 Pt 1):1-15.

Zuk et al., 2001, "Multilineage cells from human adipose tissue: implications for cell-based therapies," Tissue Eng, 7, pp. 211-228.

Aggarwal et al., 2005, "Human mesenchymal stem cells modulate allogeneic immune cell responses", Blood, 105:1815-1822.

Aitola et al., 2000, "Forkhead transcription factor FoxF2 is expressed in mesodermal tissues involved in epithelio-mesenchymal interactions", Dev. Dyn., 218:136-149.

Anderson and Young, 1985, "Quantitative Filter Hybridization" Nucleic Acid Filter Hybridization.

Badri et al., 2010, "Mesenchymal stromal cells in bronchoalveolar lavage as predictors of bronchiolitis obliterans syndrome", American Journal of Respiratory and Critical Care Medicine, 183(8): 1062-70 (Abstract Only).

Bruno et al., 2009, "Isolation and characterization of resident mesenchymal stem cells in human glomeruli," Stem Cells Dev, 18, pp. 867-880.

Bucala et al., 1994, "Circulating fibrocytes define a new leukocyte subpopulation that mediates tissue repair", Mol. Med., 1:71-81.

Castro-Malaspina et al., 1980, "Characterization of human bone marrow fibroblast colony-forming cells (CFU-F) and their progeny", Blood 56:289-301.

Chang et al., 2002, "Diversity, topographic differentiation, and positional memory in human fibroblasts", PNAS, 99:12877-12882.

Christie et al., 2008, "Registry of the International Society for Heart and Lung Transplantation: twenty-fifth official adult lung and heart/lung transplantation report—2008," J Heart Lung Transplant, 27, pp. 957-969.

Codarri et al., 2007, "Expansion and tissue infiltration of an allospecific CD4+CD25+CD45RO+1L-7Ralphahigh cell population in solid organ transplant recipients", J. Exp. Med. 204:1533-1541.

Costa et al., 2001, "Transcription factors in mouse lung development and function", Am. J. Physiol. Lung Cell Mol. Physiol., 280:L823-838.

Dazzi et al., 2006, "The role of mesenchymal stem cells in haemopoiesis," Blood Rev, 20, pp. 161-171.

Debari et al., 2001, "Multipotent mesenchymal stem cells from adult human synovial membrane," Arthritis Rheum, 44, pp. 1928-1942.

Di Bonzo et al., 2008, "Human mesenchymal stem cells as a two-edged sword in hepatic regenerative medicine: engraftment and hepatocyte differentiation versus profibrogenic potential", Gut 57:223-231.

Digiovine et al., 1996, "Bronchoalveolar lavage neutrophilia is associated with obliterative bronchiolitis after lung transplantation: role of IL-8", J. Immunol. 157:4194-4202.

Dolgachev et al., 2009, "Role of stem cell factor and bone marrow-derived fibroblasts in airway remodeling", Am. J. Pathol., 174:390-400.

Elssner et al., 2000, "Elevated levels of interleukin-8 and transforming growth factor-beta in bronchoalveolar lavage fluid from patients with bronchiolitis obliterans syndrome: proinflammatory role of bronchial epithelial cells. Munich Lung Transplant Group", Transplantation 70:362-367.

Estenne et al., 2002, "Bronchiolitis obliterans after human lung transplantation", Am. J. Respir. Crit. Care Med. 166:440-444.

Estenne et al., 2002, "Bronchiolitis obliterans syndrome 2001: an update of the diagnostic criteria", J. Heart Lung Transpl. 21:297-310.

Fuehrer et al., 2009, "Presence of c-KIT-positive mast cells in obliterative bronchiolitis from diverse causes", Archives of Pathology & Laboratory Medicine, 133(9): 1420-25.

Gabbiana, 1981, "The myofibroblast: a key cell for wound healing and fibrocontractive diseases", Prog. Clin. Biol. Res. 54:183-194.

Gerson et al, "Mesenchymal stem cells: no longer second class marrow citizens," Nat Med, 5, pp. 262-264 (1999).

Gottleib et al., 2008, "Long-term azithromycin for bronchiolitis obliterans syndrome after lung transplantation." Transplantation, 85:36-41.

Gupta et al., 2007, "Intrapulmonary delivery of bone marrow-derived mesenchymal stem cells improves survival and attenuates endotoxin-induced acute lung injury in mice," J Immunol, 179, pp. 1855-1863.

Hashimoto et al., 2004, "Bone marrow-derived progenitor cells in pulmonary fibrosis", J. Clin. Invest., 113:243-252.

Henke et al., 1999, "Persistent increases of BAL neutrophils as a predictor of mortality following lung transplant", Chest 115:403-409.

Hertz et al., 1992, "Obliterative bronchiolitis after lung transplantation: a fibroproliferative disorder associated with platelet-derived growth factor", PNAS USA, 89:10385-10389.

Hinz et al., 2007, "The myofibroblast: one function, multiple origins", Am. J. Pathol., 170:1807-1816.

Hoogduijn et al., 2009, "Donor-derived mesenchymal stem cells remain present and functional in the transplanted human heart," Am J Transplant, 9, pp. 222-230.

Huang et al., 2007, "Prostaglandin E(2) inhibits collagen expression and proliferation in patient-derived normal lung fibroblasts via E prostanoid 2 receptor and cAMP signaling", Am. J. Physiol. Lung Cell Mol. Physiol., 292:L405-413.

Humphrys et al., 2010, "Fate tracing reveals the pericyte and not epithelial origin of myofibroblasts in kidney fibrosis", Am. J. Pathol., 176:85-97.

Iwano et al., 2002, "Evidence that fibroblasts derive from epithelium during tissue fibrosis", J. Clin. Invest., 110:341-350.

Jarvinen et al., 2008, "Lung resident mesenchymal stem cells isolated from human lung allografts inhibit T-cell proliferation via a soluble mediator", Journal of Immunology, 181(6): 4389-96.

Jeon et al., 2008, "Cancer-derived lysophosphatidic acid stimulates differentiation of human mesenchymal stem cells to myofibroblast-like cells", Stem Cells 26:789-797.

Kalinichenko et al., 2001, "Defects in pulmonary vasculature and perinatal lung hemorrhage in mice heterozygous null for the Forkhead Box f1 transcription factor", Dev. Biol. 235:489-506.

Kalinichenko et al., 2004, "Foxf1 haploinsufficiency reduces Notch-2 signaling during mouse lung development", Am. J. Physiol. Lung Cell Mol. Physiol. L521-L530.

Keane et al., 2007, "IL-13 is pivotal in the fibro-obliterative process of bronchiolitis obliterans syndrome", J. Immunol., 178:511-519.

(56) References Cited

OTHER PUBLICATIONS

Keshamouni et al., 2009, "Temporal quantitative proteomics by iTRAQ 2D-LC-MS/MS and corresponding mRNA expression analysis identify post-transcriptional modulation of actin-cytoskeleton regulators during TGF-beta-Induced epithelial-mesenchymal transition", J. Proteome Res., 8:35-47.

Lama et al., 2006, "Obligatory role for interleukin-13 in obstructive lesion development in airway allografts", Am. J. Pathol. 169:47-60.

Lama et al., 2007, "Evidence for tissue-resident mesenchymal stem cells in human adult lung from studies of transplanted allografts." J Clin Invest, 117:989-996.

Lama, 2009, "Update in lung transplantation 2008." Am. J. Respir Crit Care Med, 179:759-764.

Lehmann et al., 2003, "Fox's in development and disease", Trends Genetics 19:339-344.

Liang et al., 1986, "Longitudinal data analysis using generalized linear models", Biometrika, 73:13-22.

Lim et al., 2002, "Fusion of lung lobes and vessels in mouse embryos heterozygous for the forkhead box f1 targeted allele", Am. J. Physiol. Lung Cell Mol. Physiol. 282:L1012-L1022.

Maeda et al., 2007, "Transcriptional control of lung morphogenesis", Physiol. Rev. 87:219-244.

Mahlapuu et al., 2001, "Haploinsuffciency of the forkhead gene Foxf1, a target for sonic hedgehog signaling, causes lung and foregut malformations", Development 128:2397-2406.

Mahlapuu et al., 2001, "The forkhead transcription factor Foxf1 is required for differentiation of extra-embryonic and lateral plate mesoderm", Development, 128-155-166.

Mandeville et al., 2006, "Impact of the loss of Hoxa5 function on lung alveogenesis", Am. J. Pathol., 169:1312-1327.

Mangi et al., 2003, "Mesenchymal stem cells modified with Akt prevent remodeling and restore performance of infarcted hearts", Nat. Med. 9:1195-1201.

Meyer, 2007, "Bronchoalveolar lavage as a diagnostic tool", Semin. Respir. Crit. Care Med. 28:546-560.

\* cited by examiner

SEQUENCE LISTING

```
<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
atggaattcg cgtcgtccgg cccgt                                 25

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
gggccaagct ttccacgttg cccgg                                 25
```

US 8,637,232 B2

BIOMARKERS FOR LUNG DISEASE MONITORING

This invention was made with government support under grant number HL077719 awarded by the National Institutes of Health. The government has certain rights in the invention.

FIELD OF THE INVENTION

The present invention pertains to the monitoring and treatment of lung transplant recipients. In particular, the invention pertains to the use of biomarkers to predict or detect post-lung transplantation complications (e.g., organ rejection, acute organ rejection, organ injury, bronchiolitis obliterans, bronchiolitis obliterans syndrome, organizing pneumonia), fibroproliferative repair responses, interstitial lung diseases (e.g., idiopathic pulmonary fibrosis and other fibrotic lung diseases), and other immune-mediated lung diseases (e.g., graft versus host disease, scleroderma).

BACKGROUND OF THE INVENTION

Lung transplantation is an accepted modality of treatment for advanced stage lung disease. Since the early 1990s, more than 25,000 lung transplants have been performed at centers around the world. Patients with advanced stage pulmonary disease have multiple causes of respiratory failure including chronic obstructive pulmonary disease (COPD), restrictive lung diseases including idiopathic pulmonary fibrosis (IPD), cystic fibrosis (CF), alpha1-antitrypsin disease, primary pulmonary hypertension, and various less common causes. Patients are considered for lung transplantation when life expectancy is not predicted to exceed 24-36 months despite optimal and maximal medical management and they have class III and IV New York Heart Association (NYHA) symptoms.

However, while transplantation is an appropriate lifesaving measure for some patients, in addition to the considerable economic and social cost of lung transplantation, the long-term survival statistics for transplant recipients poses a sobering burden. The International Society for Heart and Lung Transplantation Registry reports a 1-year survival rate of 78% and 5-year survival rate of 51% following lung transplantation (Christie et al. (2008) J Heart Lung Transplant. 27:957-969). Mortality is highest in the first year, and attrition is consistent across the subsequent time periods. A major cause of transplant rejection is bronchiolitis obliterans syndrome (BOS), a lung disease characterized by fixed airway obstruction. The reported incidence of BOS is 51% by 5.6 years post-transplant, as stated in the 2008 ISHLT registry report (Lama (2009) Am. J. Respir. Crit. Care Med. 179:759-764; herein incorporated by reference in its entirety). BOS is correlated with inflammation and scarring occurring in the airways of the lung, resulting in severe shortness of breath and dry cough. Whereas patients with noncompromised lungs have FEV1 (forced expiratory volume in 1 second) values of 80% of predicted values, bronchiolitis obliterans reduces FEV1 to 16% to 21%.

Treatment options for BOS are extremely limited. Late-stage BOS is largely refractory to therapy, and thus BOS is the most common indication for re-transplantation, accounting for 52% of all re-transplantation cases (Lama (2009) Am. J. Respir. Crit. Care Med. 179:759-764; herein incorporated by reference in its entirety). Modest success has been reported for treatment of early-stage BOS with azithromycin (Lama (2009) Am. J. Respir. Crit. Care Med. 179:759-764; Gottleib et al. (2008) 85:36-41). However, there is a dearth of reliable diagnostic tests capable of detecting early-stage BOS. Better methods are needed to predict risk of BOS, occurrence of early-stage BOS, and risk or occurrence of other immunological or injury-associated causes of lung transplant rejection.

SUMMARY OF THE INVENTION

The present invention pertains to the monitoring and treatment of lung transplant recipients. In particular, the invention pertains to the use of biomarkers to predict or detect post-lung transplantation complications (e.g., organ rejection, acute organ rejection, organ injury, bronchiolitis obliterans, bronchiolitis obliterans syndrome, organizing pneumonia), fibroproliferative repair responses, interstitial lung diseases (e.g., idiopathic pulmonary fibrosis and other fibrotic lung diseases), and other immune-mediated lung diseases (e.g., graft versus host disease, scleroderma).

There exists in the art a need for improved testing methods for detection of risk or presence of lung disease, particularly in clinical care of lung transplant recipients. For example, commonly occurring lung transplant complications include numerous injury- and/or immune-mediated events, diseases, and conditions (e.g., organ rejection, acute organ rejection, organ injury, bronchiolitis obliterans, bronchiolitis obliterans syndrome, organizing pneumonia). In experiments conducted during the course of developing some embodiments of the present invention, biomarkers were found that are predictive of risk of or presence of early stages of injury- or immune-mediated lung diseases or conditions in transplant patients, e.g., bronchiolitis obliterans, bronchiolitis obliterans syndrome. While the present invention is not limited to any particular mechanism, and an understanding of the mechanism is not necessary to practice the present invention, it is contemplated that the presence of lung-resident mesenchymal stem cells (LR-MSCs) is indicative of lung injury and/or immune-mediated lung disease, e.g., in transplant patients. Persistently elevated LR-MSCs (e.g., as detected in fluid samples collected from lungs of transplant patients (e.g., from BAL samples)) finds use in predicting or diagnosing post-transplant lung injury and/or immune-mediated lung disease (e.g., organ rejection, acute organ rejection, organ injury, bronchiolitis obliterans, bronchiolitis obliterans syndrome, organizing pneumonia). Surrogate biomarkers for LR-MSCs include but are not limited to RNA, protein, downstream targets, or metabolites related to biomarkers (e.g., transcription factors) expressed at high levels in LR-MSCs. Therefore, analyzing levels of such biomarkers, whether considered singly or in combination, and whether analyzed in terms of absolute level or in relation to control levels, finds use in assessing risk of or presence of lung injury and/or immune-mediated lung disease, e.g., in transplant patients. Such biomarkers include, but are not limited to, FOXF1, FOXF2, HOXA5, HOXB5, HOXB6, HOXA10, HOXC10, HOXC6, and HOXA9.

Numerous biomarker testing assays find use in some embodiments of the present invention. For example, in some embodiments, the risk of or presence of lung disorders arising from lung injury or immunological disease (e.g., organ rejection, acute organ rejection, organ injury, bronchiolitis obliterans, bronchiolitis obliterans syndrome, organizing pneumonia) is tested or monitored by assessing the presence or absence of LR-MSCs on the basis of cell phenotype (e.g., collection and analysis of cell samples (e.g., from BAL fluid) followed by analysis of growth phenotype in culture (e.g., adherence to tissue culture plastic; formation of distinct CFU-Fs; multipotency) (Lama et al. (2007) J. Clin. Invest. 117:989-

996; herein incorporated by reference in its entirety). In some embodiments, the presence or absence of LR-MSCs is assessed on the basis of presence or absence of cell surface markers (immunophenotyping) upon, e.g., collection and analysis of cell samples (e.g., from BAL fluid). For example, cells suspected to be LR-MSCs may be identified on the basis of presence of markers CD73, CD90, CD105; absence of markers CD14, CD34, and CD45; or any combination thereof (Lama et al. (2007) J. Clin. Invest. 117:989-996; herein incorporated by reference in its entirety). Methods of the present invention are not limited to particular LR-MSC biomarkers. LR-MSC biomarkers include, but are not limited to, LR-MSC cell surface markers (e.g., CD74, CD90, CD105); α-SMA; collagen I; FOX genes (e.g., FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO2, FOXO3, FOXO4, FOXP1, FOXP2, FOXP3, FOXP4, FOXQ1, FOXR1, and FOXR2); HOX genes (e.g., HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, HOXB13, HOXC4, HOXC5, HOXC6, HOXC8, HOXC9, HOXC10, HOXC11, HOXC12, HOXC13, HOXD1, HOXD3, HOXD4, HOXD8, HOXD9, HOXD10, HOXD11, HOXD12, HOXD13). Analysis of cell surface markers may be performed immunocytochemically (e.g., using immunofluorescence microscopy, fluorescence-activated cell sorting (FACS), bead-based assays (e.g., Luminex® assays).)

In some embodiments, the risk of or presence of lung disorders arising from lung injury or immunological disease (e.g., organ rejection, acute organ rejection, organ injury, bronchiolitis obliterans, bronchiolitis obliterans syndrome, organizing pneumonia) is tested or monitored by assessing the presence or absence of biomarkers described herein, whether assessed singly or in combination. Biomarkers may comprise RNA molecules (e.g., mRNA transcripts and fragments or splice variants thereof), proteins (e.g., intact proteins, modified proteins, variants and fragments thereof), and metabolites whose levels are directly or indirectly correlated with biomarker activity. Methods to determine presence or absence of RNA biomarkers include but are not limited to RT-PCR, rapid RT-PCR, multiplex RT-PCR, nuclease protection assays, in situ hybridization, in situ RT-PCR Northern blot, microarrays, SAGE, cDNA sequencing, and mass spectrometry-based methods. Methods to determine presence or absence of protein biomarkers include but are not limited to immunoassays relying on antibodies recognizing a protein biomarker of interest (e.g., enzyme-linked immunosorbant assays (ELISA), lateral flow tests, western blots, microparticle-based assays (e.g., Luminex® assays), magnetic immunoassays, dot blots, enzyme immunoassays (EIA), radioimmunoassay (RIA), chemiluminescent immunoassays (CLIA), counting immunoassays (CIA), and the like) (see, e.g., Wild et al. (2005) "The Immunoassay Handbook, 3$^{rd}$ Ed.", Elsevier Ltd., Oxford, UK). Methods to determine presence or absence of protein biomarkers may also include non-immunological techniques (e.g., mass spectrometric-based methods; enzymatic assays). Methods to detect metabolite biomarkers include but are not limited to mass spectrometric methods, enzymatic methods (e.g., utilizing an enzyme capable of binding and/or acting upon a biomarker of interest), chromatographic methods (e.g., utilizing affinity media capable of binding a metabolite biomarker of interest), and immunological methods (e.g., utilizing an antibody capable of binding to a metabolite biomarker of interest).

The level of biomarker(s) present in a sample may be assessed on an absolute basis or a relative basis. When assessed on a relative basis, comparison may be made to controls including but not limited to a historical sample from the same patient (e.g., serial samples, longitudinal samples); level(s) found in a patient or population of patients absent of disease or disorder; level(s) found in a sample (e.g., a tissue sample) from an unaffected region (e.g., non-infected region, non-diseased region) of the same patient (e.g., an unaffected lobe of a transplanted lung).

Methods of the present invention are not limited by temporal aspects of biomarker testing. Biomarker assessment may be done once, twice, three times, four times, five times, 5-10 times, 10-20 times, 20 times or more. Testing of lung transplant recipients may be performed at any time pre- or post-transplant. In some embodiments, testing occurs within three months of transplantation. In some preferred embodiments, testing occurs 3 months or more following transplantation. Methods of the present invention are not limited by combination with other tests or procedures. Biomarkers may be assessed singly or in combination (e.g., in multiplex; in serial).

Methods of the present invention are not limited by sample type. Samples may include but are not limited to tissue (e.g., organ (e.g., heart, liver, brain, lung, stomach, intestine, spleen, kidney, pancreas, and reproductive (e.g., ovaries) organs; lung biopsy), glandular, skin, and muscle tissue), cell (e.g., blood cell (e.g., lymphocyte or erythrocyte), muscle cell, tumor cell, bronchial cell, bronchioalveolar cells, and skin cell), gas, bodily fluid (e.g., tracheal aspirate fluid, bronchoalveolar fluid, bronchoalveolar lavage sample, blood or portion thereof, serum, plasma, urine, semen, saliva, etc), or solid (e.g., stool) samples obtained from a human (e.g., adult, infant, or embryo) or animal (e.g., cattle, poultry, mouse, rat, dog, pig, cat, horse, and the like). Biological samples also include biopsies and tissue sections (e.g., biopsy or section of tumor, growth, rash, infection, or paraffin-embedded sections), medical or hospital samples (e.g., including, but not limited to, bronchoalveolar lavage fluid (BAL) samples, tracheal aspirate fluid, blood samples, saliva, buccal swab, cerebrospinal fluid, pleural fluid, milk, colostrum, lymph, sputum, vomitus, bile, semen, oocytes, cervical cells, amniotic fluid, urine, stool, hair and sweat), and laboratory samples (e.g., subcellular fractions). In some preferred embodiments, samples include lung-derived samples (e.g., bronchoalveolar lavage (BAL) fluid, tracheal aspirate fluid, lung tissue samples, lung biopsy samples, sputum samples).

Biomarkers finding use in some methods and kits of the present invention include but are not limited to members of the Forkhead gene family and products thereof (e.g., transcripts, splice variants, and fragments thereof; proteins, modified proteins, variants and fragments thereof) (e.g., FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO2, FOXO3, FOXO4, FOXP1, FOXP2, FOXP3, FOXP4, FOXQ1, FOXR1, and FOXR2) and members of the Homeobox gene family and products thereof (e.g., transcripts, splice variants, and fragments thereof; proteins, modified proteins, variants and fragments thereof) (e.g., HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, HOXB13, HOXC4, HOXC5, HOXC6, HOXC8, HOXC9, HOXC10, HOXC11, HOXC12, HOXC13, HOXD1, HOXD3, HOXD4, HOXD8, HOXD9, HOXD10, HOXD11, HOXD12, HOXD13).

In some embodiments, a patient is tested to assess presence, absence, or level of biomarkers described herein to determine risk of or presence of injury- and/or immune-mediated events, diseases, and conditions (e.g., organ rejection, acute organ rejection, organ injury, bronchiolitis obliterans, bronchiolitis obliterans syndrome, organizing pneumonia), and thereafter treated based on the outcome of such test. In some embodiments, a patient is tested, treated, and then tested again to monitor response to therapy. In some embodiments, cycles of testing and treatment may occur without limitation to the pattern (e.g., test/treat/test/treat, test/treat/test/treat/test, test/treat/treat/test/treat/treat), periodicity, or duration of interval between each testing and treatment phase.

In some embodiments, the method comprises determining the level of RNA or protein product of 2, 3, 4, 5, 6-10, 11-20, 21-25, 26-30, 31-50, 51-100, 101-145 or more biomarkers described herein. In another embodiment the method comprises determining the level of RNA or protein product of all the biomarkers described herein.

In certain embodiments, the present invention provides a method for assessing risk of a lung disorder in a subject, comprising: obtaining a sample from the lungs of the subject, and assessing the level of lung-resident mesenchymal stem cells in the sample, wherein said level of mesenchymal stem cells corresponds to the risk of lung disorder occurring in the subject. In some embodiments, the lung disorder is a disorder such as organ rejection, acute organ rejection, organ injury, bronchiolitis obliterans, bronchiolitis obliterans syndrome, organizing pneumonia, fibroproliferative repair responses, graft versus host disease, interstitial lung diseases (e.g., idiopathic pulmonary fibrosis and other fibrotic lung diseases), and scleroderma. In some embodiments, assessment of the level of lung-resident mesenchymal stem cells comprises isolating cells from said lung sample and quantifying cell phenotypes such as adherence to tissue culture plastic, presence of distinct fibroblast colony forming units, multipotency, presence of one or more markers such as CD73, CF90, CD105, and absence of one or more markers such as CD14, CD34, and CD45. In some embodiments, the subject is human. In some embodiments, the subject is a lung transplant recipient. In some embodiments, the sample is a type such as a bronchoalveolar lavage fluid sample, a lung tissue sample, and a tracheal aspirate fluid sample.

In certain embodiments, the present invention provides a method for assessing presence of a lung disorder in a subject, comprising: obtaining a sample from the lungs of the subject, and assessing the level of lung-resident mesenchymal stem cells in the sample, wherein the level of mesenchymal stem cells corresponds to the risk of lung disorder occurring in the subject. In some embodiments, the lung disorder is a disorder such as organ rejection, acute organ rejection, organ injury, bronchiolitis obliterans, bronchiolitis obliterans syndrome, organizing pneumonia, fibroproliferative repair responses, graft versus host disease, interstitial lung diseases (e.g., idiopathic pulmonary fibrosis and other fibrotic lung diseases), and scleroderma. In some embodiments, assessment of the level of lung-resident mesenchymal stem cells comprises isolating cells from said lung sample and quantifying cell phenotypes such as adherence to tissue culture plastic, presence of distinct fibroblast colony forming units, multipotency, presence of one or more markers such as CD73, CF90, CD105, and absence of one or more markers such as CD14, CD34, and CD45. In some embodiments, the subject is human. In some embodiments, the subject is a lung transplant recipient. In some embodiments, the sample is a type such as a bronchoalveolar lavage fluid sample, a lung tissue sample, and a tracheal aspirate fluid sample.

In certain embodiments, the present invention provides a method for assessing risk of a lung disorder in a subject, comprising: obtaining a sample from the lungs of the subject, and assessing the level of a biomarker in the sample, the biomarker of a type such as a product of a FOX gene and a product of a HOX gene, wherein the level of biomarker corresponds to the risk of lung disorder occurring in the subject. In some embodiments, the lung disorder is a disorder such as organ rejection, acute organ rejection, organ injury, bronchiolitis obliterans, bronchiolitis obliterans syndrome, organizing pneumonia, fibroproliferative repair responses, graft versus host disease, and scleroderma. In some embodiments, the FOX gene product biomarker is a biomarker such as FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO2, FOXO3, FOXO4, FOXP1, FOXP2, FOXP3, FOXP4, FOXQ1, FOXR1, and FOXR2. In some embodiments, the FOX gene product biomarker is a type such as FOXF1 and FOXF2. In some embodiments, the HOX gene product biomarker is a type such as HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, HOXB13, HOXC4, HOXC5, HOXC6, HOXC8, HOXC9, HOXC10, HOXC11, HOXC12, HOXC13, HOXD1, HOXD3, HOXD4, HOXD8, HOXD9, HOXD10, HOXD11, HOXD12, and HOXD13. In some embodiments, the HOX gene product biomarker is a type such as HOXA5, HOXB5, HOXB6, HOXA10, HOXC10, HOXC6, and HOXA9. In some embodiments, the gene product is a type such as an RNA transcript, splice variant, or fragment thereof; and a protein product, modified protein, variant, or fragment thereof. In some embodiments, the subject is human. In some embodiments, the subject is a lung transplant recipient. In some embodiments, the sample is a type such as a bronchoalveolar lavage fluid sample, a lung tissue sample, and a tracheal aspirate fluid sample.

In certain embodiments, the present invention provides a method for assessing presence of a lung disorder in a subject, comprising: obtaining a sample from the lungs of the subject, and assessing the level of a biomarker in the sample, the biomarker of a type such as a product of a FOX gene and a product of a HOX gene, wherein the level of biomarker corresponds to the risk of lung disorder occurring in the subject. In some embodiments, the lung disorder is a disorder such as organ rejection, acute organ rejection, organ injury, bronchiolitis obliterans, bronchiolitis obliterans syndrome, organizing pneumonia, fibroproliferative repair responses, graft versus host disease, and scleroderma. In some embodiments, the FOX gene product biomarker is a biomarker such as FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO2, FOXO3, FOXO4, FOXP1, FOXP2, FOXP3, FOXP4, FOXQ1, FOXR1, and FOXR2. In some embodiments, the FOX gene product biomarker is a biomarker such as FOXF1 and FOXF2. In some embodiments, the HOX gene product biomarker is a biomarker such as HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, HOXB13, HOXC4, HOXC5, HOXC6, HOXC8, HOXC9, HOXC10, HOXC11, HOXC12, HOXC13, HOXD1, HOXD3, HOXD4, HOXD8, HOXD9, HOXD10, HOXD11, HOXD12, and HOXD13. In some embodiments, the HOX gene product biomarker is a biomarker such as HOXA5, HOXB5, HOXB6, HOXA10, HOXC10, HOXC6, and HOXA9. In some embodiments, the gene product is a product such as an RNA transcript, splice variant, or fragment thereof and a protein product, modified protein, variant, or fragment thereof. In some embodiments, the subject is human. In some embodiments, the subject is a lung transplant recipient. In some embodiments, the sample is a sample such as a bronchoalveolar lavage fluid sample, a lung tissue sample, and tracheal aspirate fluid.

In certain embodiments, the present invention provides a kit for detecting the risk of a lung disorder in a subject comprising reagents for analysis of presence or absence of a biomarker in a sample from the subject, wherein the biomarker is a type such as a product of a FOX gene and a product of a HOX gene. In some embodiments, the reagents are reagents such as probes, antibodies, and affinity media capable of binding to the gene product. In some embodiments, the FOX gene product biomarker is a biomarker such as FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO2, FOXO3, FOXO4, FOXP1, FOXP2, FOXP3, FOXP4, FOXQ1, FOXR1, and FOXR2. In some embodiments, the FOX gene product biomarker is a biomarker such as FOXF1 and FOXF2. In some embodiments, the HOX gene product biomarker is a biomarker such as HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, HOXB13, HOXC4, HOXC5, HOXC6, HOXC8, HOXC9, HOXC10, HOXC11, HOXC12, HOXC13, HOXD1, HOXD3, HOXD4, HOXD8, HOXD9, HOXD10, HOXD11, HOXD12, and HOXD13. In some embodiments, the HOX gene product biomarker is a biomarker such as HOXA5, HOXB5, HOXB6, HOXA10, HOXC10, HOXC6, and HOXA9. In some embodiments, the gene product is a product such as an RNA transcript, splice variant, or fragment thereof; and a protein product, modified protein, variant, or fragment thereof.

In certain embodiments, the present invention provides a method of assessing risk of a lung disorder in a subject, comprising: a) obtaining a lung-derived sample from the subject; and b) assessing the level of a biomarker in the sample, the biomarker of a type such as a product of a FOX gene or a product of a HOX gene, wherein the level of the biomarker corresponds to the risk of said lung disorder occurring in the subject. In some embodiments, the subject is a lung transplant recipient. In some embodiments, the lung disorder is a type such as organ rejection, acute organ rejection, organ injury, bronchiolitis obliterans, bronchiolitis obliterans syndrome, organizing pneumonia, fibroproliferative repair responses, graft versus host disease, idiopathic pulmonary fibrosis, or scleroderma. In some embodiments, the lung disorder is bronchiolitis obliterans. In some embodiments, the FOX gene is a gene such as FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO2, FOXO3, FOXO4, FOXP1, FOXP2, FOXP3, FOXP4, FOXQ1, FOXR1, or FOXR2. In some embodiments, the FOX gene is FOXF1. In some embodiments, the HOX gene is a gene such as HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, HOXB13, HOXC4, HOXC5, HOXC6, HOXC8, HOXC9, HOXC10, HOXC11, HOXC12, HOXC13, HOXD1, HOXD3, HOXD4, HOXD8, HOXD9, HOXD10, HOXD11, HOXD12, or HOXD13. In some embodiments, the HOX gene is a gene such as HOXA5, HOXB5, HOXB6, HOXA10, HOXC10, HOXC6, or HOXA9. In some embodiments, the level of the biomarker correlates to the level of lung resident-mesenchymal stem cells in the sample. In some embodiments, the product of a FOX gene or product of a HOX gene is a product such as an RNA transcript, splice variant, or fragment thereof; or a protein product, modified protein, variant, or fragment thereof. In some embodiments, the subject is human. In some embodiments, the lung-derived sample is a type such as a bronchoalveolar lavage fluid sample, a lung tissue sample, or tracheal aspirate fluid sample. In some embodiments, the subject received a lung transplant at least 3 months prior to the collection of the lung-derived sample.

In certain embodiments, the present invention provides a method of assessing the risk of bronchiolitis obliterans in a subject that has received a transplanted lung at least 3 months prior, comprising: a) obtaining a bronchoalveolar lavage fluid sample from the subject; b) isolating nucleated cells from the sample; c) culturing the isolated cells; and d) determining the number of single separated fibroblastoid colonies in the cultures, wherein a number of single separated fibroblastoid colonies of at least 10 colonies per $2 \times 10^6$ of the isolated nucleated cells correlates to increased risk of the subject developing bronchiolitis obliterans.

In certain embodiments, the present invention provides kits for detecting the risk of a lung disorder in a subject comprising reagents for analysis of presence of a biomarker for lung-resident mesenchymal stem cells in a sample from the subject. In some embodiments, the biomarker is a type such as a product of a FOX gene or a product of a HOX gene.

In certain embodiments, the present invention provides a method of assessing risk of a lung disorder in a subject, comprising obtaining a lung-derived sample from the subject; and assessing the level of a lung-resident mesenchymal stem cell biomarker in the sample, wherein the level of the biomarker corresponds to the risk of the lung disorder occurring in the subject.

In certain embodiments, the present invention provides a method of assessing the risk of a lung disorder in a subject, comprising a) obtaining a lung-derived sample from the subject; b) determining the number of lung-resident mesenchymal stem cells in the sample; and c) determining the risk of the lung disorder in the subject where an increased level of lung-resident mesenchymal stem cells in the sample correlates to increased risk of the subject having the lung disorder.

In certain embodiments, the present invention provides a kit for detecting the risk of a lung disorder in a subject comprising reagents for determining the presence of a lung-resident mesenchymal stem cell biomarker in a sample from the subject.

Additional embodiments will be apparent to persons skilled in the relevant art based on the teachings contained herein.

DEFINITIONS

Figure 1:
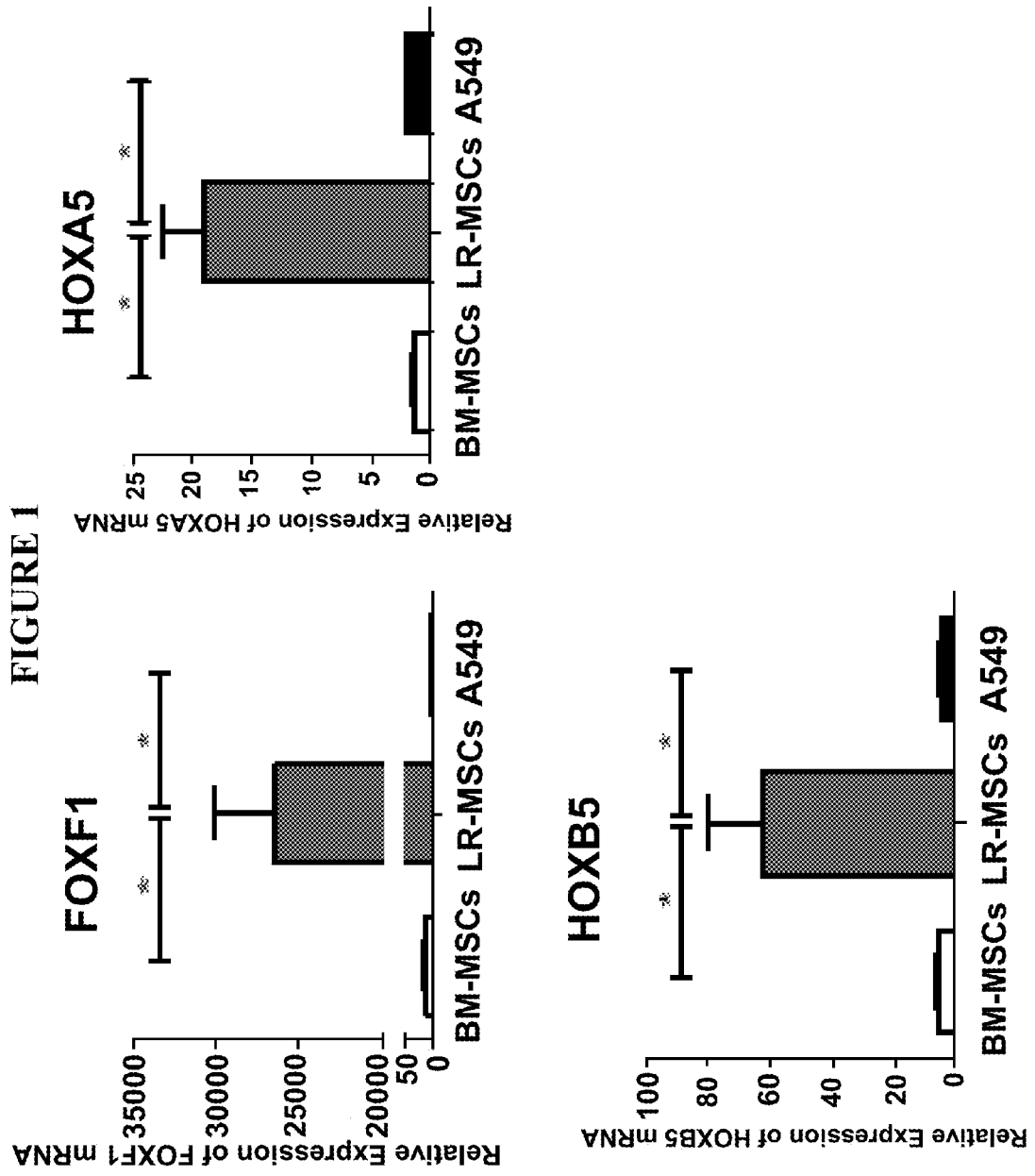
FIG. 1 shows increased expression of embryonic lung mesenchyme associated transcription factors in lung-derived mesenchymal stem cells. mRNA expression of various transcription factors in lung-resident MSCs (LR-MSCs) isolated from bronchoalveolar lavage fluid of lung allografts was compared to bone marrow-derived MSCs (BM-MSCs) by real-time PCR. mRNA expression was also compared to human lung epithelial cells (A549). * P<0.05

To facilitate an understanding of the present invention, a number of terms and phrases are defined below:

As used herein, the term "transplant rejection" refers to a partial or complete destruction (e.g., functional and/or structural) of a transplanted cell, tissue, organ, or the like on or in a recipient of said transplant (e.g., due to an immune response generated by the recipient).

As used herein, the term "tolerance" refers to the absence of transplant rejection (e.g., the absence of a recipient immune response to the transplanted graft). "Peripheral tolerance" refers generally to tolerance acquired by mature lymphocytes in peripheral tissues.

As used herein, the term "host" refers to an organism (preferably the organism is a mammal), a tissue, organ, or the like that is the recipient of a transplanted cell, tissue, organ, or the like. The terms "host" and "recipient", when referring to transplant hosts or recipients are used interchangeably, unless indicated otherwise herein.

As used herein, the term "isolated" when used in relation to material (e.g., a cell) refers to a material that is identified and separated from at least one component or contaminant with which it is ordinarily associated in its natural source. An isolated material is such present in a form or setting that is different from that in which it is found in nature.

As used herein, the term "transplantation" refers to the process of taking a cell, tissue, organ, or the like, herein called a "transplant" or "graft" from one subject and placing the transplant into a (usually) different subject. The subject that provides the transplant is called the "donor" and the subject that receives the transplant is called the "host" or "recipient". Typically, the host (i.e., the recipient of the transplant or graft; referred to herein as "graft recipient" or "transplant recipient") is a mammal, such as a human. The transplant can include any transplantable cell, tissue, organ or the like. For example, it can include a kidney, liver, heart, lung, bone marrow, skin, etc. Thus, a graft wherein the donor and host are genetically identical is a syngeneic graft. Where the donor and host are the same subject, the graft is called an autograft. The invention relates to all types of grafts. In certain embodiments, the invention relates to lung transplants (including but not limited to partial lung transplants, single lung transplants, double lung transplants, heart-lung transplants.)

As used herein, the terms "immunoglobulin" and "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like (e.g., that is to be the recipient of a particular treatment (e.g., transplant graft) or that is a donor of a graft. The terms "subject" and "patient" are used interchangeably in reference to a human subject, unless indicated otherwise herein (e.g., wherein a subject is a graft donor).

As used herein, the term "predicting transplant rejection risk in a subject" refers to determining the risk of a subject rejecting a transplant (e.g., graft tissue, cell, organ or the like) at any point following the transplant.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "in vitro" refers to an artificial environment and to processes or reactions that occur within an artificial environment. In vitro environments include, but are not limited to, test tubes and cell culture. The term "in vivo" refers to the natural environment (e.g., an animal or a cell) and to processes or reaction that occur within a natural environment.

As used herein, the term "sample" is used in its broadest sense. For example, in some embodiments, it is meant to include a specimen (e.g., bronchoalveolar lavage sample) or culture (e.g., cell culture). In preferred embodiments, it is meant to include a biological sample.

The present invention is not limited by the type of biological sample used or analyzed. The present invention is useful with a variety of biological samples including, but are not limited to, tissue (e.g., organ (e.g., lung, heart, liver, brain, stomach, intestine, spleen, kidney, pancreas, and reproductive (e.g., ovaries) organs; lung biopsy), glandular, skin, and muscle tissue), cell (e.g., blood cell (e.g., lymphocyte or erythrocyte), muscle cell, tumor cell, bronchial cell, bronchioalveolar cells, and skin cell), gas, bodily fluid (e.g., tracheal aspirate fluid, bronchoalveolar fluid, bronchoalveolar lavage sample, blood or portion thereof, serum, plasma, urine, semen, saliva, etc), or solid (e.g., stool) samples obtained from a human (e.g., adult, infant, or embryo) or animal (e.g., cattle, poultry, mouse, rat, dog, pig, cat, horse, and the like). Biological samples may be obtained from all of the various families of domestic animals, as well as feral or wild animals, including, but not limited to, such animals as ungulates, bear, fish, lagomorphs, rodents, etc.

Biological samples also include biopsies and tissue sections (e.g., biopsy or section of tumor, growth, rash, infection, or paraffin-embedded sections), medical or hospital samples (e.g., including, but not limited to, bronchoalveolar lavage fluid (BAL) samples, tracheal aspirate fluid, blood samples, saliva, buccal swab, cerebrospinal fluid, pleural fluid, milk, colostrum, lymph, sputum, vomitus, bile, semen, oocytes, cervical cells, amniotic fluid, urine, stool, hair and sweat), and laboratory samples (e.g., subcellular fractions).

As used herein, the term "bronchoalveolar lavage" or "BAL" refers to any medical procedure in which fluid (e.g., saline) is administered to a portion of a lung and re-collected for analysis. Upon re-collection, BAL fluid samples may contain biological components including but not limited to cells (e.g., lung-resident mesenchymal stem cells, T-cells, bacterial cells, fungal cells) and non-cellular substances (e.g., cytokines, viruses, RNA, cellular protein, secreted protein, metabolites). Typically, a bronchoscope is used for administration and collection of BAL fluid. BAL procedures and the samples obtained thereby are not limited by the region of the lung to which fluid is administered, the type of fluid administered, the volume of fluid administered, or any other aspects of the procedure (e.g., co-administration of anesthetic or antibiotic agents).

As used herein, the term "differentially expressed" or "differential expression" refers to a difference in the level of expression of biomarkers of some embodiments of the invention. Such difference can be assayed by measuring the level of expression of the products of biomarkers of some embodiments of the invention, such as the difference in level of RNA (e.g., mRNA) or protein expressed. The term "difference in the level of expression" refers to an increase or decrease in the measurable expression level of a given biomarker as measured by the amount of RNA or protein in a sample as compared with the measurable expression level of a given biomarker in a second sample. The term can also refer to an increase or decrease in the measurable expression level of a given biomarker in a population of samples as compared with the measurable expression level of a biomarker in a second population of samples. In one embodiment, the differential expression can be compared using the ratio of the level of expression of a given biomarker(s) as compared with the expression level of the given biomarker(s) of a control, wherein the ratio is not equal to 1.0. For example, an RNA or protein molecule is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment, the differential expression is measured using p-value associated with outcome of a statistical test. For instance, when using p-value, a biomarker is identified as being differentially expressed as between a first and second population when the p-value is less than 0.1, preferably less than 0.05, more preferably less than 0.01, even more preferably less than 0.005, the most preferably less than 0.001.

As used herein, the term "risk of primary graft failure" refers to a risk of donor lung failure in the transplantation recipient. Primary graft failure is a major cause of early death after lung transplantation.

As used herein, the term "biomarker" refers to a gene, gene product, cell type, metabolite, RNA (e.g., mRNA), protein, or fragment or variant thereof that is differentially present or differentially expressed in donor lungs that are at risk as compared to not at risk of post-transplant complications (e.g., primary graft failure, organ rejection, acute organ rejection, organ injury, bronchiolitis obliterans, bronchiolitis obliterans syndrome, organizing pneumonia).

As used herein, the phrase "screening for, diagnosing or detecting risk" refers to a method or process of determining if an organ (e.g., donor lung) or patient (e.g., transplant recipient) is at risk or not at risk of an undesired outcome (e.g., if a donor lung is at risk of primary graft failure, if a transplant recipient is at risk of a post-transplant complication (e.g., primary graft failure, organ rejection, acute organ rejection, organ injury, bronchiolitis obliterans, bronchiolitis obliterans syndrome, organizing pneumonia)).

As used herein, the term "RNA products of the biomarkers" refers to RNA transcripts transcribed from genes utilized as biomarkers in some embodiments of the invention. The term "RNA product" of some gene biomarker embodiments of the invention as used herein includes mRNA transcripts, and/or specific spliced variants, fragments, or derivatives thereof.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

A gene, such as a gene encoding a biomarker for lung-resident mesenchymal stem cells (e.g., FOXF1), may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity, they will both hybridize to a probe derived from the entire gene or portions of the gene containing sequences found on both cDNAs; the two splice variants are therefore substantially homologous to such a probe and to each other.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. In certain embodiments, a probe used in the present invention will be labeled with a "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.)

and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$(% G+C), when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5.times. Denhardt's reagent and 100. mu.g/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5x.SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×.SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in Nucleic Acid Hybridization (1985) and Sambrook et al., Molecular Cloning: A Laboratory Manual, Cold Spring Harbor Press, NY (1989)).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, Adv. Appl. Math. 2: 482 (1981)] by the homology alignment algorithm of Needleman and Wunsch [Needleman and Wunsch, J. Mol. Biol. 48:443 (1970)], by the search for similarity method of Pearson and Lipman [Pearson and Lipman, Proc. Natl. Acad. Sci. (U.S.A.) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

As used herein, the term "lung-derived sample" means a biological sample generated by, including, or obtained from cells, tissues, organs, or fluid in the respiratory system. Examples of lung-derived samples include, but are not limited to, bronchoalveolar lavage fluid samples, lung tissue samples, and tracheal aspirate fluid samples.

DETAILED DESCRIPTION OF THE INVENTION

Mesenchymal stem cells (MSCs) are a unique subset of adult progenitor cells (Gerson et al. (1999) Nat. Med. 5:262-264; Pittenger et al. (1999) Science 284:143-147; each herein incorporated by reference in its entirety) which can be isolated from a wide variety of human tissues and organs (De Bari et al. (2001) Arthritis Rheum. 44:1928-1942; Noth et al. (2002) J. Orthop. Res. 20:1060-1069; Pierdomenico et al. (2005) Transplantation 80:836-842; Sabatini et al. (2005) Lab Invest. 85:962-671; Young et al. (2001) Anat. Rec. 264: 51-62; Zuk et al. (2001) Tissue Eng. 7:211-228; each herein incorporated by reference in its entirety). MSCs can modulate the local microenvironment by both secretion of soluble factors and trans-differentiation into various connective tissue lineages (Gupta et al. (2007) J. Immunol. 179:1855-1863; Ortiz et al. (2003) PNAS USA 100:8407-8411; Rasmusson (2006) Exp. Cell. Res. 312:2169-2179; Uccelli et al. (2007) Trends Immunol. 28:219-226; each herein incorporated by reference in its entirety). The most commonly described source of MSCs is the bone marrow, where MSCs are thought to be critical elements of the hematopoetic stem cell niche (Dazzi et al. (2006) Blood Rev. 20:161-171; herein incorporated by reference in its entirety).

By studying donor vs. recipient origin of MSCs in transplanted solid organs, it has been demonstrated that MSCs are resident in postnatal, non-hematopoetic organs in humans (Bruno et al. (2009) Stem Cells Dev. 18:867-880; Hoogduijn et al. (2009) Am J. Transplant 9:222-230; Lama et al. (2007) J. Clin. Invest. 117:989-996; each herein incorporated by reference in its entirety). These tissue-resident MSCs are a reservoir of endogenous mesenchymal progenitor cells; however, their role in tissue repair and disease pathogenesis during adult life in solid organs is not known.

Lung transplantation across an allogeneic barrier provokes a cascade of organized and disorganized reparative responses and offers a unique opportunity to study cells involved in these processes. Donor lung demonstrates significant resilience, with normal repair ensuing in the majority of instances following the ischemia/reperfusion insult associated with implantation. However, a maladaptive repair response to repeated immune and non-immune injuries in the post-transplant period can lead to mesenchymal cell proliferation and differentiation manifesting as fibrotic obliteration of small airways, a process termed bronchiolitis obliterans (BO) (Estenne et al. (2002) Am. J. Respir. Crit. Care Med. 166:440-444; herein incorporated by reference in its entirety). This physiological consequence of BO is an inability to exhale, measured as a decline in FEV1, and this parameter defines bronchiolitis obliterans syndrome (BOS) (Estenne et al. (2002) J. Heart Lung Transplant 21:297-310; herein incorporated by reference in its entirety). While BOS continues to be the major cause of graft failure after lung transplantation (Christie et al. (2008) J. Heart Lung Transplant 27:957-696; herein incorporated by reference in its entirety), pathogenesis of fibrosis in BOS in not well understood (Estenne et al. (2002) Am. J. Respir. Crit. Care Med. 166:440-444). Similarly, in spite of the ability to safely and reproducibly sample the internal milieu of the lung by fiberoptic bronchoscopy (Meyer (2007) Semin. Respir. Crit. Care Med. 28:546-560; Tiroke et al. (1999) Clin. Transplant 13:131-157; each herein incorporated by reference in its entirety), predictors of BOS in bronchoalveolar lavage (BAL) have not been established (Estenne et al. (2002) J. Heart Lung Transplant 21:297-310; Wilkes et al. (2005) Am. J. Respir. Crit. Care Med. 172:944-955; each herein incorporated by reference in its entirety).

Donor-derived MSCs can be isolated from the lower respiratory tract of human lung transplant recipients by BAL (Lama et al. (2007) J. Clin. Invest. 117:989-996; herein incorporated by reference in its entirety). In experiments conducted during the course of developing some embodiments of the present invention, the ability to isolate MSCs from an easily accessible source such as BAL in a clinical scenario associated with intense immunological insult was utilized to determine the role of MSCs in human lung injury. Lung-resident MSCs (LR-MSCs) expand in response to injury, and experiments conducted during the course of developing some embodiments of the present invention show that an increased number of LR-MSCs in the BAL predicts BOS onset in human lung transplant recipients. Additionally, studies conducted during the course of developing some embodiments of the present invention demonstrate a unique expression of embryonic lung mesenchymal transcription factor in LR-MSCs, indicating their lung-specificity and contribution to fibrogenesis post-transplantation.

Data presented herein (see Examples) provide evidence supporting the role of organ-specific endogenous mesenchymal progenitor cells in tissue repair and disease pathogenesis in humans. LR-MSCs derived from the human lung allografts demonstrate unique expression of specific transcription factors seen in embryonic lung mesenchyme. LR-MSC demonstrated 35,000-fold higher expression of FOXF1, a transcription factor expressed specifically in the mesenchyme of the developing lung, when compared to BM-MSCs (e.g., see Example 2). While the present invention is not limited to any particular mechanism, and an understanding of the mechanism is not necessary to practice the present invention, it is contemplated that these tissue-derived MSCs are remnants of embryonic lung mesenchyme and hence are tissue-specific. By studying the kinetics of LR-MSC accumulation in BAL samples following transplantation, it was shown that the number of these mesenchymal progenitor cells increases significantly in association with histological or physiological evidence of injury, indicating a role for these cells in regulating tissue injury or tissue repair responses. Increased numbers of LR-MSCs in BAL greater than 6 months after transplantation was found to be a strong predictor of future decline in lung function, demonstrating that MSC accumulation precedes and predicts BOS onset. This finding, while providing a clue to the role of LR-MSCs in BOS pathogenesis, has even more significance as a biomarker of chronic rejection in human lung transplant recipients. Additionally, by studying biopsies obtained from lung transplant recipients, it was demonstrated that myofibroblasts in fibrotic lesion also express lung mesenchymal transcription factor FOXF1, hence showing that these cells originate from local remnant mesenchymal progenitor cells. Together, these data provide evidence for the presence and role of tissue-specific, organ-resident mesenchymal stem cells in reparative responses and disease pathogenesis in humans. While the present invention is not limited to any particular mechanism, and an understanding of the mechanism is not necessary to practice the present invention, it is contemplated that endogenous progenitor cells have an important role in tissue repair, and increased understanding of these cells is critical in understanding and impacting disease pathogenesis.

In vitro studies and studies based on administration of exogenous MSCs have demonstrated the ability of MSCs to modulate the local microenvironment (Gupta et al. (2007) J. Immunol. 179:1855-1863; Ortiz et al. (2003) PNAS USA 100:8407-8411; Mangi et al. (2003) Nat. Med. 9:1195-1201; Miyahara et al. (2006) Nat. Med. 12:459-465; Nemeth et al. (2009) Nat. Med. 15:42-49; Rojas et al. (2005) Am. J. Respir. Cell Mol. Biol. 33:145-152; each herein incorporated by reference in its entirety). However, the in vivo role of endogenous MSCs is not well-established. This is especially true for solid organs such as the lung, where the role, if any, of endogenous MSCs was unknown prior to experiments conducted during the course of developing some embodiments of the present invention. The ability to isolate MSCs from an easily accessible source such as BAL in a clinical scenario associated with intense immunological insult affords a unique opportunity to investigate the role of MSCs in human lung injury. Several clinical variables influenced the number of LR-MSCs in the lung allografts. Increased numbers of LR-MSCs were associated with histological evidence of rejection on concurrent transbronchial biopsies. Increased numbers of LR-MSCs were also seen early post-transplantation; a time after transplant of greater than 3 months significantly predicted a lower BAL CFU-F count. Elevated total cell counts in BAL have been reported during the first 3 months after lung transplantation, a period marked by both reperfusion injury and an intense allo-immune response (Tiroke et al. (1999) Clin. Transplant 13:131-157; herein incorporated by reference in its entirety). The correlation of increased LR-MSCs with these clinical variables clearly demonstrates that LR-MSCs expand in response to injury. Furthermore, the donor origin and unique expression of lung embryonic mesenchymal transcription factor in LR-MSCs demonstrates that these cells are organ-specific endogenous progenitor cells. Experiments conducted during the course of developing some embodiments of the present invention identified novel cellular markers of rejection arising from the graft itself. Determination of allo-injury in solid organ transplants presently relies on measuring infiltration of recipient-derived hematopoetic cells in the transplanted organ (Codarri et al. (2007) J. Exp. Med. 204:1533-1541; Studer et al. (2008) Am. J. Respir. Crit. Care Med. 178:765-773; each herein incorporated by reference in its entirety). The demonstration that cellular response of the graft is a key marker of allo-injury presents a novel paradigm that has not been investigated previously in any solid organ transplant.

Increased numbers of LR-MSCs in BAL fluid was shown find use as a predictor of BOS onset. Predicting BOS early, prior to clinical compromise, enables modification of immunosuppressive and other therapeutic modalities to prevent or delay BOS onset. Since bronchoscopy is a minimally invasive procedure used routinely in clinical transplant medicine, BAL samples are an available source to analyze biomarkers. Previous methods have utilized neutrophils in BAL samples as predictors of BOS (DiGiovine et al. (1996) J. Immunol. 157:4194-4202; Henke et al. (1999) Chest 115:403-409; Riise et al. (1999) Eur. J. Respir. J. 14:1123-1130; Elssner et al. (2000) Transplantation 70:362-367; each herein incorporated by reference in its entirety). Such analysis is however of low clinical value due to low specificity, as BALF neutrophilia can be caused by infection. In the cohort used in some experiments conducted during the course of developing some embodiments of the present invention, increased numbers of neutrophils were seen in the presence of positive bacterial cultures in the BAL. However, no correlation was seen between number of LR-MSCs in BAL and positive bacterial cultures, demonstrating that LR-MSCs are a superior indicator of cellular response to non-infectious inflammatory processes. In some embodiments, the present invention provides easily measurable, potent, cellular biomarkers of BOS onset, addressing a crucial area of unmet need in the clinical field of lung transplantation.

An important question is whether LR-MSCs play a role in the pathogenesis of BOS. MSCs have strong immuno-modulating properties (Rasmusson (2006) Exp. Cell Res. 312: 2169-2179; Uccelli et al. (2007) Trends Immunol. 28:219-226; each herein incorporated by reference in its entirety) and LR-MSCs derived from human lung allografts inhibit T cells in vitro via secretion of soluble mediators (Jarvinen et al. (2008) J. Immunol. 181:4389-4396; herein incorporated by reference in its entirety). Exogenous administration of BM-MSCs ameliorates injury in animal lung injury models via their ability to modulate the local immune microenvironment (Gupta et al. (2007) J. Immunol. 179:1855-1863; Ortiz et al. (2003) PNAS USA 100:8407-8411; Rojas et al. (2005) Am. J. Respir. Cell Mol. Biol. 33:145-152; each herein incorporated by reference in its entirety). While these studies document that MSCs can modulate the local microenvironment by their secretory products to exert a beneficial anti-inflammatory effect, a potential role of MSCs in tissue fibrosis in chronic injury cannot be overlooked. The myofibroblast, the key effector cell of fibrogenesis, is an activated differentiated mesenchymal cell (Gabbianai (1981) Prog. Clin. Biol. Res. 54:183-194; herein incorporated by reference in its entirety). BM-derived MSCs can differentiate into myofibroblasts in vitro (Jeon et al. (2008) Stem Cells 26:789-797; Mishra et al. (2008) Cancer Res. 68:4331-4339; each herein incorporated by reference in its entirety). Similarly, MSCs administered in vivo in animal models of chronic injury can participate in fibrotic responses (di Bonzo et al. (2008) Gut 57:223-231; Wi et al (2005) J. Heart Lung Transplant 24:2160-2169; Ye et al. (2006) Eye 20:482-490; each herein incorporated by reference in its entirety). These observations show that MSCs can have divergent effects in acute and chronic injury scenarios. Experiments conducted during the course of developing some embodiments of the present invention investigated endogenous MSCs in human injury. Increased numbers of LR-MSCs were noted early post-transplant in patients with both favorable and unfavorable long-term outcomes, demonstrating that these cells are not associated with fibrosis during acute injury. However, increased numbers at later timepoints post-lung transplantation were associated with development of BOS. The ability of LR-MSCs to differentiate into myofibroblasts in response to TGF-β and the expression of the mesenchymal transcription factor FOXF1 in myofibroblasts indicate that LR-MSCs are the source of a portion of myofibroblasts present in fibrotic lesions seen post lung-transplantation. While the present invention is not limited to any particular mechanism, and an understanding of the mechanism is not necessary to practice the present invention, it is contemplated that LR-MSCs recruited in response to injury can be modulated by the presence of a pro-fibrotic milieu and hence contribute to fibrogenesis.

Thus, the importance of data presented herein is at least threefold. First, they demonstrate that MSCs expand in response to injury, providing evidence that endogenously-derived progenitor cells participate in tissue injury responses in adult organs. Second, this increase in LR-MSC population, which is easily measurable by bronchoscopy and BAL, is an indicator of immune mediated lung injury and fibroproliferative repair responses, a biomarker which has significant implication in other immune-mediated lung diseases such as graft versus host disease and scleroderma. Third, the kinetics of LR-MSC predictive capacity points to a unique role of the microenvironment in determining the functional significance of these cells.

In summary, embodiments of the present invention provide methods in a previously unrecognized area of the cellular responses of the graft to immune-injury in solid organ transplantation. Data presented herein indicate that measuring the cellular response of the donor organ is an even more powerful marker of immune injury and graft dysfunction than the measurement of infiltrating recipient populations. Utilizing cellular response of the graft as a harbinger of rejection marks a useful paradigm in the field of solid organ transplantation.

Lung Transplantation

Since the time of the first successful single-lung transplantation in 1983, the number of lung transplant centers as well as organ recipients has continued to rise. This trend coupled with ongoing advances in transplant medicine has led to a growing lung transplant recipient patient subset. Currently, the most common indication for lung transplantation is chronic obstructive pulmonary disease, but other common indications for lung transplantation include pulmonary hypertension, cystic fibrosis, idiopathic pulmonary fibrosis, and Eisenmenger syndrome. Four different surgical techniques are used: single-lung transplantation, bilateral sequential transplantation, combined heart-lung transplantation, and lobar transplantation, with the overwhelming majority of organs procured from deceased donors. The indications for each of these techniques are evolving and are individual to the underlying disease processes. Medical complications seen in lung transplant recipients are variable and most importantly may be a result of surgical complications, graft rejection, or immunosuppression, either a direct pharmacologic toxicity or an infectious etiology.

At the close of 2007, approximately 2,500 patients were awaiting lung or combined heart-lung transplantation, with transplantation programs available at nearly 70 hospitals nationwide. The mean waiting time for lung transplantation was nearly 14 months, and, in 2007, nearly 1500 patients received a donor organ. There is no defined lower limit of age for lung transplantation, and it is largely limited by the availabilities of suitable-sized donors. Because of the increasingly poor survival with advancing age, limits have been recommended: 55 years for heart-lung transplantation, 60 years for bilateral-lung transplantation, and 65 years for single-lung transplantation. In 2007, survival rates were approximately 84% at 1 year and 44% at 5 years post transplantation for a single lung, and 83% and 50% at 1 and 5 years respectively for a double lung transplant.

Surgical complications following lung transplantation can be divided into acute and chronic complications. Many of the acute complications occur while the patient is still in the inpatient postoperative setting. Acute complications include reperfusion edema, hemothorax, pleural effusions, chylothorax (a result of perioperative injury to the thoracic duct), pneumothorax, and full or partial dehiscence of the bronchial anastomosis. Delayed airway complications are commonly seen postoperatively, and they typically present several weeks to months post transplantation. These complications include stenosis of the anastomotic site, formation of granulation tissue, or bronchomalacia. Pleural space problems may also occur and include such problems as bronchopleural fistulas, loculated pleural effusions, and hemothorax or fibrothorax. Additionally, as with any other postoperative patient, lung transplant recipients are at risk for pulmonary embolus and other thromboembolic events, possibly due to a hypercoagulable state, which is of an unclear etiology.

Graft rejection may be divided into subcategories: hyperacute, acute, and chronic rejection. Hyperacute, or primary graft failure, occurs within 72 hours postoperatively. Primary graft failure results from ischemia-reperfusion injury and presents similarly to acute respiratory distress syndrome. Early mortality may reach up to 60%, and patients who survive to hospital discharge additionally have a protracted course of recovery with significant impairments in pulmonary function. Acute graft rejection is characterized by a host T-cell response toward the transplanted organ. The incidence of acute graft rejection is highest in the first 3 months, with rare cases occurring 1 year post transplantation. The diagnosis of acute rejection is made based on both clinical and histologic criteria. Clinical features are nonspecific and include dyspnea, fever, leukocytosis, nonproductive cough, hypoxemia, or malaise. Chest radiography may show new opacifications or pleural effusions, but findings are often absent after the first month. The clinical course is variable and depends on the severity of rejection; mild cases of rejection may even be asymptomatic. Diagnosis of acute graft rejection can be confirmed with bronchoscopic lung biopsy, which reveals perivascular lymphocytic infiltrates. Treatment for acute graft rejection is high-dose parenteral steroids (methylprednisolone 0.5-1 g/d IV) and should be started in consultation with a pulmonologist.

Chronic graft rejection, like acute graft rejection, is also characterized by both histologic and clinical parameters. Clinically, the symptoms of chronic rejection are nonspecific and variable in severity. In mild chronic rejection, the patient may present with a nonproductive cough and dyspnea on exertion, and it can progress to dyspnea at rest, productive cough, pseudomonas colonization, and chest radiographic findings of bronchiectasis and air trapping. Histologic changes involve either the vasculature or the airways. Chronic vascular rejection is caused by atherosclerosis of the pulmonary vasculature, while chronic airway rejection is caused by bronchiolitis obliterans. Bronchiolitis obliterans occurs more frequently and is the main source of morbidity and mortality in lung transplant patients. Histologically, bronchiolitis obliterans is a dense irreversible scarring of the terminal and respiratory bronchioles, which partially or totally obliterates the lumen of the airway causing a progressive decline in pulmonary function. Because of the poor sensitivity of transbronchial lung biopsy, perhaps as low as 15-17%, chronic graft rejection is defined as an unexplained drop in the FEV1 to a level of 80% or less of the patient's posttransplantation peak value. Other markers, such as interleukin 12 (IL-12) levels in bronchoalveolar lavage fluid and levels of exhaled nitric oxide, have been contemplated as potential markers but have as yet proven of limited clinical use. Chronic rejection rarely occurs within the first 3 months after transplantation, but its prevalence increases with time. No specific treatment exists for chronic graft rejection, and efforts are aimed toward immunosuppression and primary prevention. Clinical treatment upon presenting symptoms of allograft rejection (which are nonspecific and may present similarly to pulmonary infections) include but are not limited to chest radiograph, CBC, chemistries, evaluation of immunosuppressant levels, pulmonary function tests, bronchoscopy/BAL, and transbronchial lung biopsies.

Bronchoalveolar Lavage

Bronchoalveolar lavage (BAL) is a diagnostic procedure in which a fiber-optic bronchoscope is passed through the mouth or nose into the lung and fluid is introduced into a small part of the lung and then recollected for examination. BAL is distinguished from segmental or whole lung lavage (WLL), a therapeutic procedure most often employed in pulmonary alveolar proteinosis to wash out the proteinaceous material occluding the airspaces. In WLL, both lungs are separately intubated under general anesthesia and one lung at a time is completely and repeatedly filled to total lung capacity with saline, then gravity drained, rinsing the lung free of occlusive material.

General indications for BAL include but are not limited to non-resolving pneumonia, diffuse lung infiltrates (interstitial and/or alveolar), suspected alveolar hemorrhage, quantitative cultures for ventilator associated pneumonia, infiltrates in an immunocompromised host, research, and diagnosis of conditions including infections, alveolar hemorrhage, malignancies, bronchoalveolar carcinoma, etc.

Bronchoalveolar lavage is a minimally invasive, first-line examination of the lung parenchyma. Cytology, gram staining and culturing can be performed on the fluids collected. Many other biomarkers can be analyzed from BAL fluids, and this can assist the clinician in establishing a diagnosis, in refining differential diagnosis, and in the clinical management of the patient. BAL has a well established role in the diagnosis of pulmonary infections, particularly those due to opportunistic organisms in an immunocomprised host. As a research tool, BAL has been used to characterize the effectiveness of intravenous drug delivery to the lungs and to improve understanding of lung biology in the distal lung. The clinician is able to collect inflammatory cells and mediators for analysis. In that way, BAL has been invaluable to the understanding of disease states such as sarcoidosis and pulmonary fibrosis. For the physician, BAL has clinical utility as well. It allows the safe sampling of the distal lung for specific pathogens (for example, *Mycobacterium tuberculosis*) in patients unable to expectorate diagnostic sputum. BAL has become a simple, yet important, tool.

For focal infiltrates on the chest film, the segmental bronchus chosen for BAL should be the one in the area of new or progressive radiologic abnormality. In patients with more than one radiologic opacity, the segmental bronchus with the most purulent secretions should be chosen under direct visualization. If the infiltrates are diffuse, the lateral segment of the right middle lobe or the superior segment of the lingual are recommended, maximizing percentage of fluid recovery by the less dependent anatomy of these lobe. Lavage performed in the right middle lobe can yield up to 20 percent more fluid return compared to the lower lobes.

An exemplary BAL procedure is given; methods of the present invention are not limited by the exact BAL procedure or variants thereof employed for collecting BAL samples.

Supplies used for a BAL procedure include 0.9 percent normal saline, 250 ml; five 30-ml slip-tip syringes (BD) filled with 25 ml of normal saline (NS) and the remaining volume comprised of air; and 30-inch extension IV tubing (Hospira). In a typical BAL procedure, the fiber-optic bronchoscope is introduced into the endobronchial tree in the usual fashion, without the use of suction or introduction of lidocaine into the working channel. The scope is then advanced to a segmental bronchus and wedged in place to completely occlude the lumen. Proper wedging prevents seepage of the lavage fluid proximally, which causes irritation and cough. Preventing cough is important because this can cause trauma, contamination of blood or mucus, and loss of instillate. If the wedge is incomplete, air will be seen bubbling into the syringe. An excessively tight wedge can lead to a poorer return and unnecessary trauma to the bronchial mucosa. The "male" end of the extension set is placed into the instrument/channel suction port of the bronchoscope and held in place. The "female" end of the extension set is attached to the male end of the syringe and the NS is slowly injected through the extension set into the wedged section of the lung. Overly rapid injection can cause the patient to cough, leading to trauma and/or bleeding to the airway, especially if the platelet count is low. A second syringe is attached and injected in the same manner as the first. Once the second syringe is completely instilled, the technician will lower the syringe and the extension set below the level of the table. This allows gravity to aid in the withdrawal of the aliquot of NS. Gentle, steady suction should be applied to the syringe plunger. Uncontrolled and rapid suctioning can cause less fluid recovery and the segmental bronchial wall may collapse when all of the negative pressure is applied. After as much aspirate is obtained as possible, the third syringe of NS is instilled and then aspirated as described supra. The process is continued until all five of the 25-ml syringes full of NS have been used. Then, the last empty syringe is used to remove the remainder of excess saline from the wedged segment. The male end of the extension set is removed from the bronchoscope and the biopsy valve cover is replaced on the scope. BAL fluid samples are combined, labeled, and sent for analysis.

Lung Injury and Lung Disease States

Methods of the present invention find use in diagnosing or predicting the risk of a variety of lung disease states related to lung transplantation (e.g., organ rejection, acute organ rejection, organ injury, bronchiolitis obliterans, bronchiolitis obliterans syndrome, organizing pneumonia). In some embodiments, methods of the present invention find use in diagnosing or predicting the risk of a variety of immunologically-medicated lung diseases or disease states involving lung injury. Such lung diseases or conditions include but are not limited to fibroproliferative repair responses, graft versus host disease, interstitial lung diseases (e.g., idiopathic pulmonary fibrosis and other fibrotic lung diseases), scleroderma, asthma, chronic obstructive pulmonary disease (COPD), emphysema, chronic bronchitis, pulmonary fibrosis, hypersensitivity pneumonitis, bronchopulmonary dysplasia, respiratory distress syndrome (RDS), acute respiratory distress syndrome (ARDS), cystic fibrosis, and alpha-1 antitrypsin deficiency.

FOX and HOX Gene and Protein Families

FOX (Forkhead box) proteins are a family of transcription factors that play important roles in regulating the expression of genes involved in cell growth, proliferation, differentiation, and longevity. Many FOX proteins are important to embryonic development (Tuteja et al. (2007) Cell 130:1160; Tuteja et al. (2007) Cell 131:192; each herein incorporated by reference in its entirety). The defining feature of FOX proteins is the forkhead box, a sequence of 80 to 100 amino acids forming a motif that binds to DNA. This forkhead motif is also known as the winged helix due to the butterfly-like appearance of the loops in the protein structure of the domain (Lehmann et al. (2003) Trends Genetics 19:339-344; herein incorporated by reference in its entirety). Forkhead genes are a subgroup of the helix-turn-helix class of proteins.

Several members of the FOX family are involved in lung development and differentiation, with some (e.g., FOXA1, FOXA2) having critical roles in early embryonic lung development, while others (e.g., FOXF1, FOXM1B) are involved in development of pulmonary mesenchyme (Maeda et al. (2007) Physiol. Rev. 87:219-244; herein incorporated by reference in its entirety). Members of the FOX family include but are not limited to FOXA1, FOXA2, FOXA3, FOXB1, FOXB2, FOXC1, FOXC2, FOXD1, FOXD2, FOXD3, FOXD4, FOXD5, FOXD6, FOXE1, FOXE2, FOXE3, FOXF1, FOXF2, FOXG1, FOXH1, FOXI1, FOXI2, FOXJ1, FOXJ2, FOXJ3, FOXK1, FOXK2, FOXL1, FOXL2, FOXM1, FOXN1, FOXN2, FOXN3, FOXN4, FOXO1, FOXO2, FOXO3, FOXO4, FOXP1, FOXP2, FOXP3, FOXP4, FOXQ1, FOXR1, and FOXR2.

In some embodiments of the present invention, Forkhead box F1 (FOXF1) finds use as a biomarker for LR-MSCs and is correlated with risk of or presence of early-stage BO or BOS, whether considered singly or in combination with other biomarkers. Alternative names for *Homo sapiens* FOXF1 include but are not limited to FKHL5, Forkhead box protein F1, Forkhead-related activator 1, Forkhead-related protein FKHL5, Forkhead-related transcription factor 1, FREAC1, FREAC-1, and MGC105125. In some embodiments of the present invention, targets of FOXF1 transcriptional activation find use as biomarkers for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia). Downstream targets of FOXF1 include but are not limited to human homologs of mouse Sftpb, Vegfa, Vegfr2, Bmp-4, Tbx, Lklf; Fgf-10, Gli3, c-met, myosin VI, SP3, BMI-1, ATF-2, GR, p53, p21, RB, p107, Notch-2 receptor, and HES-1 (Maeda et al. (2007) Physiol. Rev. 87:219-244; Kalinichenko et al. (2001) Dev. Biol. 235:489-506; Lim et al. (2002) Am. J. Physiol. Lung Cell Mol. Physiol. 282:L1012-L1022; Mahlapuu et al. (2001) Development 128:2397-2406; Kalinichenko et al. (2004) Am. J. Physiol. Lung Cell Mol. Physiol. L524-L530; each herein incorporated by reference in its entirety).

In some embodiments of the present invention, Forkhead box F2 (FOXF2) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* FOXF1 include but are not limited to FKHL6, Forkhead box protein F2, Forkhead-related activator 2, Forkhead-related protein FKHL6, Forkhead-related transcription factor 2, FREAC2, and FREAC-2.

In some embodiments of the present invention, Homeobox (HOX) genes, transcripts, proteins, or variants or fragments thereof find use as biomarkers for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia). HOX genes include a homeobox region, which is about 180 base pairs long. The homeobox region encodes a protein domain (the homeodomain) which when expressed (e.g. as protein) can bind DNA. Homeobox genes encode transcription factors which typically switch on cascades of other genes. The homeodomain binds DNA in a specific manner. Typically, homeodomain proteins act in the promoter region of their target genes as complexes with other transcription factors, often also homeodomain proteins. Such complexes have higher target specificity than a single homeodomain protein. Homeodomains are found both in genes of the Hox gene clusters and in other genes throughout the genome (see Table 1).

TABLE 1

Human homeobox genes.

| name | chromosome | gene |
|---|---|---|
| HOXA (or sometimes HOX1) | 7 | HOXA1, HOXA2, HOXA3, HOXA4, HOXA5, HOXA6, HOXA7, HOXA9, HOXA10, HOXA11, HOXA13 |
| HOXB | 17 | HOXB1, HOXB2, HOXB3, HOXB4, HOXB5, HOXB6, HOXB7, HOXB8, HOXB9, HOXB13 |
| HOXC | 12 | HOXC4, HOXC5, HOXC6, HOXC8, HOXC9, HOXC10, HOXC11, HOXC12, HOXC13 |
| HOXD | 2 | HOXD1, HOXD3, HOXD4, HOXD8, HOXD9, HOXD10, HOXD11, HOXD12, HOXD13 |

In some embodiments of the present invention, Homeobox A5 (HOXA5) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* HOXA5 include but are not limited to Hox-A5, HOX1, HOX1.3, HOX1C, Hox-1C, and MGC9376.

In some embodiments of the present invention, Homeobox B5 (HOXB5) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* HOXB5 include but are not limited to HHO.C10, Homeobox protein Hox-B5, HOX2, Hox2.1, HOX2A, Hox-2A, and HU-1.

In some embodiments of the present invention, Homeobox B6 (HOXB6) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* HOXB6 include but are not limited to Homeobox protein Hox-B6, HOX2, Hox-2.2, HOX2B, Hox-2B, and HU-2.

In some embodiments of the present invention, Homeobox A10 (HOXA10) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* HOXA10 include but are not limited to Homeobox protein Hox-A10, HOX1, HOX1.8, Hox-1.8, HOX1H, Hox-1H, MGC12859, and PL.

In some embodiments of the present invention, Homeobox C10 (HOXC10) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* HOXC10 include but are not limited to Homeobox protein Hox-C10, HOX3I, and MGC5259.

In some embodiments of the present invention, Homeobox C6 (HOXC6) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* HOXC6 include but are not limited to CP25, HHO.C8, Homeobox protein Hox-C6, HOX3, HOX3C, and Hox-3C.

In some embodiments of the present invention, Homeobox A9 (HOXA9) finds use as a biomarker for LR-MSCs and/or risk of or presence of lung disorders arising from lung injury or immunological disease (e.g., organ rejection, acute organ rejection, organ injury, bronchiolitis obliterans, bronchiolitis obliterans syndrome, organizing pneumonia), whether considered singly or in combination with other biomarkers. Alternative names for *Homo sapiens* HOXA9 include but are not limited to ABD-B, Homeobox protein Hox-A9, HOX1, HOX1.7, HOX1G, Hox-1G, and MGC 1934.

Biomarker Testing Methods

Numerous biomarker testing assays find use in some embodiments of the present invention. For example, in some embodiments, the risk of or presence of lung disorders arising from lung injury or immunological disease (e.g., organ rejection, acute organ rejection, organ injury, bronchiolitis obliterans, bronchiolitis obliterans syndrome, organizing pneumonia) is tested or monitored by assessing the presence or absence of LR-MSCs on the basis of cell phenotype (e.g., collection and analysis of cell samples (e.g., from BAL fluid) followed by analysis of growth phenotype in culture (e.g., adherence to tissue culture plastic; formation of distinct CFU-Fs; multipotency) (Lama et al. (2007) J. Clin. Invest. 117:989-996; herein incorporated by reference in its entirety). In some embodiments, the presence or absence of LR-MSCs is assessed on the basis of presence or absence of cell surface markers (immunophenotyping) upon, e.g., collection and analysis of cell samples (e.g., from BAL fluid). For example, cells suspected to be LR-MSCs may be identified on the basis of presence of markers CD73, CF90, CD105 and absence of markers CD14, CD34, and CD45 (Lama et al. (2007) J. Clin. Invest. 117:989-996; herein incorporated by reference in its entirety). Analysis of cell surface markers may be performed immunocytochemically (e.g., using immunofluorescence microscopy, fluorescence-activated cell sorting (FACS), bead-based assays (e.g., Luminex® assays), etc.).

In some embodiments, the risk of or presence of lung disorders arising from lung injury or immunological disease (e.g., organ rejection, acute organ rejection, organ injury, bronchiolitis obliterans, bronchiolitis obliterans syndrome, organizing pneumonia) is tested or monitored by assessing the presence or absence of biomarkers described herein, whether assessed singly or in combination. Biomarkers may comprise RNA molecules (e.g., mRNA transcripts and fragments or splice variants thereof), proteins (e.g., intact proteins, modified proteins, variants and fragments thereof), and metabolites whose levels are directly or indirectly correlated with biomarker activity. Methods to determine presence or absence of RNA biomarkers include but are not limited to RT-PCR, multiplex RT-PCR, Northern blot, microarrays, SAGE, cDNA sequencing, and mass spectrometry-based methods. Methods to determine presence or absence of protein biomarkers include but are not limited to immunoassays relying on antibodies recognizing a protein biomarker of interest (e.g., enzyme-linked immunosorbant assays (ELISA), lateral flow tests, western blots, microparticle-based assays (e.g., Luminex® assays), magnetic immunoassays, dot blots, enzyme immunoassays (EIA), radioimmunoassay (RIA), chemiluminescent immunoassays (CLIA), counting immunoassays (CIA), and the like) (see, e.g., Wild et al. (2005) "The Immunoassay Handbook, 3$^{rd}$ Ed.", Elsevier Ltd., Oxford, UK). Immunoassays may be competitive or noncompetitive. Methods to determine presence or absence of protein biomarkers may also include non-immunological techniques (e.g., mass spectrometric-based methods; enzymatic assays). Methods to detect metabolite biomarkers include but are not limited to mass spectrometric methods, enzymatic methods (e.g., utilizing an enzyme capable of binding and/or acting upon a biomarker of interest), chromatographic methods (e.g., utilizing affinity media capable of binding a metabolite biomarker of interest), and immunological methods (e.g., utilizing an antibody capable of binding to a metabolite biomarker of interest).

The level of biomarker(s) present in a sample may be assessed on an absolute basis or a relative basis. When assessed on a relative basis, comparison may be made to controls including but not limited to a historical sample from the same patient (e.g., serial samples, longitudinal samples); level(s) found in a patient or population of patients absent of disease or disorder; level(s) found in a sample (e.g., a tissue sample) from an unaffected region (e.g., non-infected region, non-diseased region) of the same patient (e.g., an unaffected lobe of a transplanted lung).

Testing Services

In some embodiments, a computer-based analysis program is used to translate the raw data generated by the assay (e.g., RT-PCR, bead-based assay, immunoassay, mass spectrometry-based assay)) (e.g., the presence, absence, or amount of a biomarker) (e.g., LR-MSCs; transcript corresponding to a member of Forkhead gene family; FOXF1 transcript; FOXF2 transcript; transcript of a member of the Homeobox gene family; transcript of HOXA5, HOXB5, HOXB6, HOXA10, HOXC10, HOXC6, HOXA9) into data of predictive value for an end user (e.g., a physician, a patient, a healthcare practitioner). The end user can access the predictive data using any suitable means. Thus, in some embodiments, the present invention provides the further benefit that the end user, who is not likely to be trained in biomarker analysis, need not understand the raw data. The data is presented directly to the end user in its most useful form. The end user is then able to immediately utilize the information in order to optimize the care of the subject (e.g., patient).

The present invention contemplates any method capable of receiving, processing, and transmitting the information to and from laboratories conducting the assays, information pertaining to samples. For example, in some embodiments of the present invention, a sample (e.g., a BAL fluid sample) is obtained and submitted to a profiling service (e.g., laboratory etc.), located in any part of the world (e.g., in a country matching that of or different than the country where the subject resides or where the information is ultimately used) to generate raw data. The end user may have the sample (e.g., a BAL fluid sample) obtained by a third party and sent to the profiling center, or subjects may collect the sample themselves or with help of a healthcare professional and directly send it to a profiling center. Where the sample comprises previously determined information, the information may be directly sent to the profiling service by the end user (e.g., an information card containing the information may be scanned by a computer and the data transmitted to a computer of the profiling center using an electronic communication systems). Once received by the profiling service, the sample is processed and a profile is produced (e.g., biomarker content), specific for the diagnostic or prognostic information desired for the end user.

The profile data is then prepared in a format suitable for interpretation by an end user. For example, rather than providing raw data, the prepared format may represent a risk assessment (e.g., likelihood of biomarker being present) for the end user, along with recommendations for particular patient care options. The data may be displayed to the end user by any suitable method. For example, in some embodiments, the profiling service generates a report that can be printed for the end user (e.g., at the point of patient contact, at the point of patient care) or displayed to the end user on a computer monitor.

In some embodiments, the information is first analyzed at the point of patient care or at a regional facility. The raw data is then sent to a central processing facility for further analysis and/or to convert the raw data to information useful for an end user or other interested party. The central processing facility provides the advantage of privacy (all data is stored in a central facility with uniform security protocols), speed, and uniformity of data analysis. The central processing facility can then control the fate of the data following communication to the end user. For example, using an electronic communication system, the central facility can provide data to the end user.

In some embodiments, the end user is able to directly access the data using the electronic communication system. The end user may seek further advice based on the results. In some embodiments, the data is used for research use. In some embodiments, the data may be used to further optimize a treatment regime for a transplant patient (e.g., a lung transplant recipient).

EXAMPLES

The following examples are provided in order to demonstrate and further illustrate certain preferred embodiments and aspects of the present invention and are not to be construed as limiting the scope thereof.

Example 1

Resident Mesenchymal Stem Cells as Responders to Injury and Novel Markers of Rejection in Human Lung Transplants Methods
Patient Population Lung transplant recipients undergoing bronchoscopy at the University of Michigan were eligible for enrollment in the study. The study was approved by the University of Michigan Institutional Review Board, and informed consent was obtained prior to participation. Bronchoscopy and BAL with transbronchial biopsies were performed using standard techniques. BAL samples that could be maintained in culture for 14 days, hence allowing LR-MSC quantification were included in the study. The indication for bronchoscopy was defined as surveillance if it was routinely performed. Non-surveillance bronchoscopies were performed when clinically indicated for factors such as dyspnea, decrement in lung function or follow-up of previous episodes of acute rejection. Bacterial, fungal, and viral cultures were performed on all BAL samples. Transbronchial biopsies obtained at the time of BAL were examined for the presence of acute rejection or bronchiolitis obliterans according to established criteria (Yousem et al. (1996) J. Heart Lung Transpl. 15:1-15; herein incorporated by reference in its entirety). Acute rejection was defined as biopsy score of ≥A1 or B1 (Yousem et al. (1996) J. Heart Lung Transpl. 15:1-15; herein incorporated by reference in its entirety). BOS was defined by physiological testing according to the International Society of Heart and Lung Transplantation guidelines (Estenne et al. (2002) J. Heart Lung Transpl. 21:297-310; herein incorporated by reference in its entirety).

CFU-F Assay on Human BAL Samples

Bronchoalveolar lavage (BAL) samples were processed as previously described (Lama et al. (2007) J. Clin. Invest. 117: 989-996; Jarvinen et al. (2008) J. Immunol. 181:4389-4396; each herein incorporated by reference in its entirety). The numbers of fibroblast colony forming units (CFU-F) in BAL were measured using methods similar to those described by Castro-Malaspina for bone marrow-derived cells (Castro-Malaspina et al. (1980) Blood 56:289-301; herein incorporated by reference in its entirety). Recovered BAL fluid was filtered through a sterile strainer to remove non-cellular particulate material, and the cell pellet recovered by centrifugation at 1,000 rpm for 5 minutes. Two million nucleated cells isolated from BAL were seeded in a 100 mm cell culture dish and incubated at 37° C. in 5% $CO_2$/95% air in medium consisting of high-glucose DMEM supplemented with 10% fetal bovine serum (FBS) (Invitrogen), 100 U/ml penicillin/streptomycin (Invitrogen), and 0.5% fungizone (Invitrogen). Medium was changed every 2-3 days. Single separated fibroblastoid colonies were identified as early as 7 days after initial plating. Colonies were counted between days 14 and 21 after initial plating.

Affymetrix and Real-Time Quantitative PCR Analysis

Lung-resident mesenchymal stem cells (LR-MSCs) isolated from the BAL fluid were maintained in culture in DMEM with penicillin/streptomycin and 10% FCS at 37° C. in 5% $CO_2$ as previously described (Lama et al. (2007) J. Clin. Invest. 117:989-996; Jarvinen et al. (2008) J. Immunol. 181: 4389-4396; each herein incorporated by reference in its entirety). BM-MSCs were isolated from the normal human bone marrow aspirate as previously described under a protocol approved by University of Michigan Institutional Review Board (Lama et al. (2007) J. Clin. Invest. 117:989-996; herein incorporated by reference in its entirety). A549 cells were purchased from American Type Culture Collection (Manassas, Va.) and grown in Kaighn's-F12 containing 10% fetal bovine serum, 50 μg/ml penicillin, and 50 μg/ml streptomycin in 5% $CO_2$ at 37° C. Total RNA was prepared using the RNeasy mini kit (Qiagen, Inc. Valencia, Calif.) as per the manufacturer's instructions. Real-time quantitative PCR analysis was performed on an ABI Prism 7000 SDS (Applied Biosystems, Foster City, Calif.) using the TaqMan PCR Master Mix (Applied Biosystems). The TaqMan real time PCR primers were purchased from Applied Biosystems and included Hs00230962_m1 for FOXF1, Hs00430330_m1 for HOXA5, and Hs00357820_m1 for HOXB5. For Affymetrix analysis, total RNA was prepared from three sets each of bone marrow and BAL-derived MSCs cultured under similar conditions at passage 3. Affymetrix array hybridization and scanning were performed by the UMCCC Affymetrix and cDNA Microarray Core Facility, University of Michigan, Ann Arbor, Mich., USA, using Human U133 plus 2.0 chips. Expression values for each gene were calculated using a robust multiarray average and were stored as $log_2$ transformed data. Two-tailed Student's t test was used to determine differential expression of genes between lung derived and bone marrow-derived MSCs.

Immunofluorescent Staining and Western Blot Analysis

For immunofluorescent staining, LR-MSCs were trypsinized, harvested and plated at a density of 50,000 cells per 35-mm cell culture dish. Cells were allowed to adhere overnight before serum-starvation for 24 hours. Following serum-starvation, LR-MSCs were treated for 24 hours with 2 ng/mL of TGF-β (R and D Systems; Minneapolis, Minn.) in DMEM containing no serum. Following treatment, cells were fixed with ice-cold methanol for 10 minutes and blocked with PBS containing 1.5% Bovine Serum Albumin, 1.5% goat serum, and 0.5% Triton X-100. Dishes were incubated overnight at 4° C. with mouse monoclonal anti-α-SMA (clone 1A4, Dako), followed by staining with AlexaFluor 488 conjugated anti-mouse secondary (Invitrogen, Eugene, Oreg.) and DAPI nuclear stain.

For western blot analysis, LR-MSCs were plated at a density of 200,000 cells per 60-mm dish and subsequently serum-starved and treated with TGF-β at described above. Controls were cells grown in serum-free media only. Protein was harvested from control and TGF-β dishes using Cell Lytic M Buffer (Sigma) containing 10% protease inhibitor cocktail (Sigma) following a PBS wash. Lysate total protein concentration was determined using a Coomassie protein assay. Equal amounts of protein were prepared for each sample by mixing a 1:1 volume ratio of protein to Laemmli buffer (Bio-Rad) containing β-mercaptoethanol, followed by heat denaturation at 97° C. for 3 minutes. SDS-Polyacrylamide gel electrophoresis was performed using a 10% polyacrylamide gel, followed by electrophoretic transfer onto a PVDF membrane. Membrane was blocked for 1 hour with 7% non-fat milk in TBS-Tween followed by incubation with mouse monoclonal anti-α-SMA diluted in blocking buffer (clone 1A4, Dako) at 4° C. overnight. Membrane was washed and incubated with rabbit polyclonal anti-GAPDH for 1 hour followed by incubation with AlexaFluor 680 conjugated anti rabbit secondary (Invitrogen) and IRDye800 conjugated anti-mouse secondary (Rockland). Membrane was washed and analyzed using an Odyssey fluorescence imager (Licor).

Immunohistochemical Staining and In-Situ Hybridization

Three patients in this cohort had histological diagnosis of a fibrotic process on transbronchial biopsies (2 with pathological diagnosis of organizing pneumonia and one with diagnosis of proliferative bronchiolitis obliterans). Paraffin-embedded sections from these biopsies were recovered under an institutional review board-approved protocol. Staining with α-SMA antibodies (Sigma-Aldrich, St. Louis, Mo.) was done according to standard clinical laboratory procedure as previously described (Lama et al. (2006) Am. J. Pathol. 169:47-60; herein incorporated by reference in its entirety).

FOXF1 Generation FOXF1 DIG-Labeled RNA Probe:

Human FOXF1 ORFeome Collaboration Clone (I.D.1000-67187, Accession # EU832158) was purchased from Open Biosystems (Huntsville, Ala.). Bacterial colonies containing FOXF1 vector were grown, selected on the basis of kanamycin resistance, and DNA was extracted according to manufacturer's protocol using a Qiagen mini prep kit (Valencia, Calif.). DNA was amplified by polymerase chain reaction (PCR) using human FOXF1 primers containing EcoR1 and Hind III cutting sites (forward and reverse respectively) from Integrated DNA Technologies (Coralville, Iowa) (forward primer: 5' ATG GAA TTC GCG TCG TCC GGC CCG T 3' (SEQ ID NO:1); reverse primer: 5' GGG CCA AGC TTT CCA CGT TGC CCG G 3' (SEQ ID NO:2). Purified DNA was then labeled with DIG according to manufacturer's protocol using DIG RNA labeling kit (SP6/T7) from Roche Applied Science (Penzberg, Germany).

In Situ Hybridization

In Situ Hybridization was performed according to manufacturer's protocol using an In Situ Hybridization kit purchased from Biochain Institute Inc. (Hayward, Calif.). All reagents were freshly made and treated with DEPC as necessary prior to use. Slides were deparaffinized with xylene twice, rehydrated in different concentrations of ethanol (100%, 90%, 80% and 70% respectively) and washed in distilled water. Slides were fixed with 4% paraformaldehyde for 20 minutes at room temperature and washed twice with PBS. Sections were digested with (20 μg/ml) proteinase K (Invitrogen, Carlsbad, Calif.) at 37° C. for 20 minutes, washed with PBS, fixed again with 4% paraformadehyde for 15 minutes and rinsed with water. Slides were incubated with pre-hybridization solution (supplied with the kit) for 4 hours at 50° C. DIG labeled FOXF1 probe was added to the hybridization solution and slides were hybridized for 16 hours at 45° C. Slides were washed, blocked for 2 hours and incubated with alkaline phosphatase conjugated anti-DIG antibody overnight at 4° C. Slides were washed with alkaline phosphotase buffer and color was developed using Fast Red TR/Napthol AS-MX (Sigma, Saint Louis, Mo.).

Data Analysis

The Wilcoxon signed-rank test was used to compare pairwise differences in continuous CFU-F counts between aliquots from the same BAL sample. A one sample t-test was used to test that CFU-F between serial dilutions decreased by 50% on average. Wilcoxon rank sum tests were used to compare CFU-F counts between cases and controls at various time-points post-lung transplantation. Poisson generalized estimating equations (GEE) were used to determine which clinical variables predict CFUF counts in BAL samples; this model accounts for correlation between BAL samples taken serially from the same individual (Liang et al. (1986) Biometrika 73:13-22; herein incorporated by reference in its entirety). GEEs were also used to determine association of various BAL cell populations (% neutrophils, % histiocytes and % lymphocytes) with CFU-F counts. Time to BOS was modeled using Cox proportional hazards models with robust variance estimation used to account for patients contributing more than one event history from various BAL measurements. CFU-group specific adjusted times to BOS plots for the average patient profile were taken from corresponding Cox models.

Results

LR-MSCs Demonstrate a Distinct Profile of Mesenchymal Transcription Factor Expression Consistent with a Local Derivation MSCs derived from human lung allografts are donor in origin, demonstrating that these are lung-resident cells (Lama et al. (2007) J. Clin. Invest. 117:989-996; herein incorporated by reference in its entirety). However, whether LR-MSCs represent a tissue-specific cell or potential remnants of embryonic lung mesenchyme was unknown prior to experiments conducted during the course of developing some embodiments of the present invention.

Distinct transcription factors are expressed in the developing lung mesenchyme (Costa et al. (2001) Am. J. Physiol. Lung Cell Mol. Physiol. 280:L823-838; herein incorporated by reference in its entirety). Of these, the best studied is the mesenchyme-specific forkhead box gene FOXF1 (also known as HFH-8 or Freac-1). FOXF1 is expressed in the splanchnic mesoderm during organogenesis (Peterson et al. (1997) Mech. Dev. 69:53-69; herein incorporated by reference in its entirety) and its expression is essential for lung development (Kalinichenko et al. (2001) Dev. Biol. 235:489-506; Lim et al. (2002) Am. J. Physiol. Lung Cell Mol. Physiol. 282:L1012-1022; Mahlapuu et al. (2001) Development 128: 2397-2406; Mahlapuu et al. (2001) Development 128:155-166; each herein incorporated by reference in its entirety). In the homeodomain HOX family, expression of HOXA5 and HOXB5 genes in the embryonic mesenchyme of the developing lung is necessary for normal branching morphogenesis (Mandeville et al. (2006) Am. J. Pathol. 169:1312-1327; Volpe et al. (1997) Histochem. Cell Biol. 108:495-504; Volpe et al. (2003) Birth Defects Res. A Clin. Mol. Teratol. 67:550-556; Volpe et al. (2000) Biochim. Biophys. Acta 1475:337-345; each herein incorporated by reference in its entirety), and genetic deletion of HOXA5 leads to respiratory tract defects (Mandeville et al. (2006) Am. J. Pathol. 169:1312-1327; herein incorporated by reference in its entirety).

To determine whether this unique expression of transcription factors is present in lung-derived MSCs, the gene expression profile of LR-MSCs was compared with bone marrow-derived MSCs (BM-MSCs) by Affymetrix analysis (Table 2). Significantly higher expression of FOXF1 was seen in LR-MSCs compared to BM-MSCs. FOXF2 or FREAC-2, another gene from the forkhead family which is expressed along with FOXF1 in mesodermal tissues of the developing and adult lungs (Aitola et al. (2000) Dev. Dyn. 218:136-149; Pierrou et al. (1994) EMBO J. 13:5002-5012; each herein incorporated by reference in its entirety), was also found to be upregulated in LR-MSCs compared to BM-MSCs (Table 2). Using a P value threshold of 0.01 and a 3 fold expression change cutoff, 7 HOX genes were found to be differentially expressed between LR-MSCs and BM-MSCs. Three HOX genes (HOXA5, HOXB5 and HOXB6) demonstrated an increased expression as compared to BM-MSCs. The most highly expressed HOX gene in BM-MSCs compared to LR-MSCs was HOXA9, a gene whose expression has been shown to be critical in haematopoesis (Chiba (1998) Int. J. Hematol. 68:343-353; herein incorporated by reference in its entirety).

TABLE 2

Comparison of selected gene expression between lung- and bone marrow-derived mesenchymal stem cells by Affymetrix analysis.

| Gene Title | Gene Symbol | p | Fold[A] | Expression Value[B] | | | | | |
|---|---|---|---|---|---|---|---|---|---|
| | | | | LR 1 | LR 2 | LR 3 | BM 1 | BM 2 | BM 3 |
| forkhead box F1 | FOXF1 | 0.001 | 5.4 | 10.48 | 8.69 | 7.62 | 3.29 | 3.52 | 3.95 |
| forkhead box F2 | FOXF2 | <0.001 | 3.3 | 9.87 | 8.78 | 9.43 | 6.12 | 6.07 | 6.05 |
| homeobox A5 | HOXA5 | <0.001 | 4.0 | 10.19 | 10.22 | 10.97 | 6.42 | 6.37 | 6.62 |
| homeobox B5 | HOXB5 | <0.001 | 3.3 | 9.97 | 8.99 | 8.73 | 5.86 | 5.87 | 6.04 |
| homeobox B6 | HOXB6 | <0.001 | 3.2 | 9.22 | 9.25 | 0.31 | 6.09 | 5.97 | 6.20 |
| homeobox A9 | HOXA9 | <0.001 | −3.3 | 4.79 | 4.79 | 6.02 | 8.52 | 8.73 | 8.35 |
| homeobox A10 | HOXA10 | <0.001 | −3.4 | 3.96 | 3.93 | 4.19 | 7.84 | 7.66 | 6.85 |
| homeobox C10 | HOXC10 | <0.001 | −3.9 | 4.56 | 4.70 | 4.50 | 8.34 | 8.47 | 8.61 |

TABLE 2-continued

Comparison of selected gene expression between lung- and bone marrow-derived mesenchymal stem cells by Affymetrix analysis.

| Gene Title | Gene Symbol | p | Fold[A] | Expression Value[B] | | | | | |
|---|---|---|---|---|---|---|---|---|---|
| | | | | LR 1 | LR 2 | LR 3 | BM 1 | BM 2 | BM 3 |
| homeobox C6 | HOXE6 | 0.001 | −4.8 | 4.25 | 5.86 | 6.76 | 10.31 | 10.55 | 10.45 |
| homeobox A9 | HOXA9 | <0.001 | −6.0 | 3.55 | 3.48 | 4.00 | 9.71 | 9.76 | 9.54 |

[A]indicates fold difference, lung vs. bone marrow-derived mesenchymal stem cells.
[B]indicates expression values that are $\log_2$ transformed data.
BM, human bone marrow-derived MSCs.
LR, human long allograft-derived MSCs.

Real-time PCR analysis confirmed increased expression of FOXF1, HOXA5 and HOXB5 in LR-MSCs compared to BM-MSCs (FIG. 1). Data presented herein demonstrate a 2,700-fold increased expression of FOXF1 in LR-MSCs than in BM-MSCs (p=0.002). FOXF1 is specifically expressed only in the mesenchyme, and real-time PCR also demonstrated a 27,000 fold increased expression of FOXF1 in LR-MSCs as compared to human alveolar epithelial cell line A549. Furthermore, a 19-fold increased expression of HOXA5 (P=0.006) and a 11-fold increased expression of HOXB5 (p=0.03) was noted in LR-MSCs compared to BM-MSCs. While the present invention is not limited to any particular mechanism, and an understanding of the mechanism is not necessary to practice the present invention, it is contemplated that this unique expression of fetal lung mesenchyme associated transcription factors in LR-MSCs isolated from adult lungs indicates that LR-MSCs are derived from embryonic mesenchyme and represent a local resident progenitor cell.

Lung Resident-MSCs Expands in Response to Injury

To determine whether this endogenous population of MSCs is mobilized during injury, the number of LR-MSCs in BAL fluid obtained from lung allografts was quantified and correlation with clinical variables was analyzed. The LR-MSC population in the BAL was quantitated using the colony forming unit-fibroblast (CFU-F) assay as described supra. LR-MSC quantification was performed in 177 bronchoalveolar lavage (BAL) fluid samples from 92 lung transplant recipients. The patient population included 40 females and 52 males with a mean age of 48 years (range, 21-69 years) at the time of transplantation. Major indications for transplantation included emphysema (n=38), idiopathic pulmonary fibrosis (n=29), cystic fibrosis (n=11), primary pulmonary hypertension (n=4), lymphangioleiomyomatosis (n=3), and other diagnoses (n=7). Characteristics of the BAL samples are detailed in Table 3.

TABLE 3

Characteristics of bronchoalveolar lavage samples (N = 177).

| Clinical Variable | N (%) |
|---|---|
| Indication for bronchoscopy | |
| Surveillance | 115 (64.97) |
| Time from Transplant to BAL | |
| 0-3 months | 38 (21.47) |
| 3-6 months | 33 (18.64) |
| 6 months-1 year | 40 (22.60) |
| 1-2 years | 39 (22.03) |
| >2 years | 27 (15.25) |
| Biopsy at the time of BAL | |
| Normal | 138 (77.96) |
| Acute rejection | 35 (19.77) |
| Bronchiolitis Obliterans/Organizing pneumonia | 3 (1.69) |
| Others | 1 (0.56) |
| BOS stage at the time of BAL | |
| BOS 0 | 151 (85.31) |
| BOS 1 or more | 26 (14.69) |
| Microbiology Cultures from BAL | |
| Positive bacterial cultures | 15 (8.47) |
| Positive CMV viral cultures | 11 (6.21) |
| Positive respiratory viral cultures | 3 (1.69) |

CFU-F counts per $2\times10^6$ cells plated in a 100 mm dish were reported. To determine that the quantification technique was valid, cells obtained from 15 BAL samples were plated in duplicate ($2\times10^6$ million cells per dish, two separate 100 mm dishes) and CFU-F counts were obtained for each dish in a given patient. There were no statistically significant differences between aliquots (Wilcoxon signed rank test p=0.44). Further serial two-fold dilutions were performed on 5 BAL samples. An average of 51% decrease in CFU-F counts (range 40% to 60%) was noted between serial dilutions. This decrease was not significantly different from 50% according to one sample t-test (p=0.94). These analyses showed reproducibility between measures of CFU-F count from a BAL sample and support the quantitative nature of the CFU-F assay.

Figure 2:
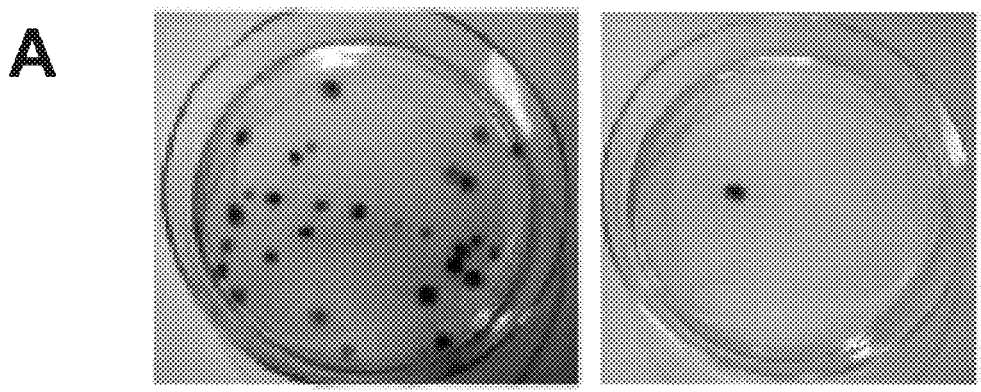
FIG. 2 shows an example of variability in the number of LR-MSCs in bronchoalveolar lavage fluid (BAL) from lung transplant recipients and its correlation with clinical status. (A), Representative samples demonstrating variability in the number of LR-MSCs in BAL. LR-MSCs were quantitated in the BAL obtained from human lung transplant recipient by colony forming unit-fibroblast (CFU-F) assay. Left panel demonstrates CFU-F count of 28 identified by Giemsa staining at day 14 in BAL sample obtained from a patient with acute rejection. Right panel demonstrates CFU-F count of 1 in a control BAL. (B), Mean CFU-F in BAL of lung transplant recipients grouped by their clinical status demonstrated by time after lung transplantation. Controls (squares) are BAL samples with no concurrent evidence of rejection or BOS. Cases (diamonds) consist of BAL samples with either concurrent presence of histological rejection or diagnosis of BOS within 6 months of BAL.
Figure 2:
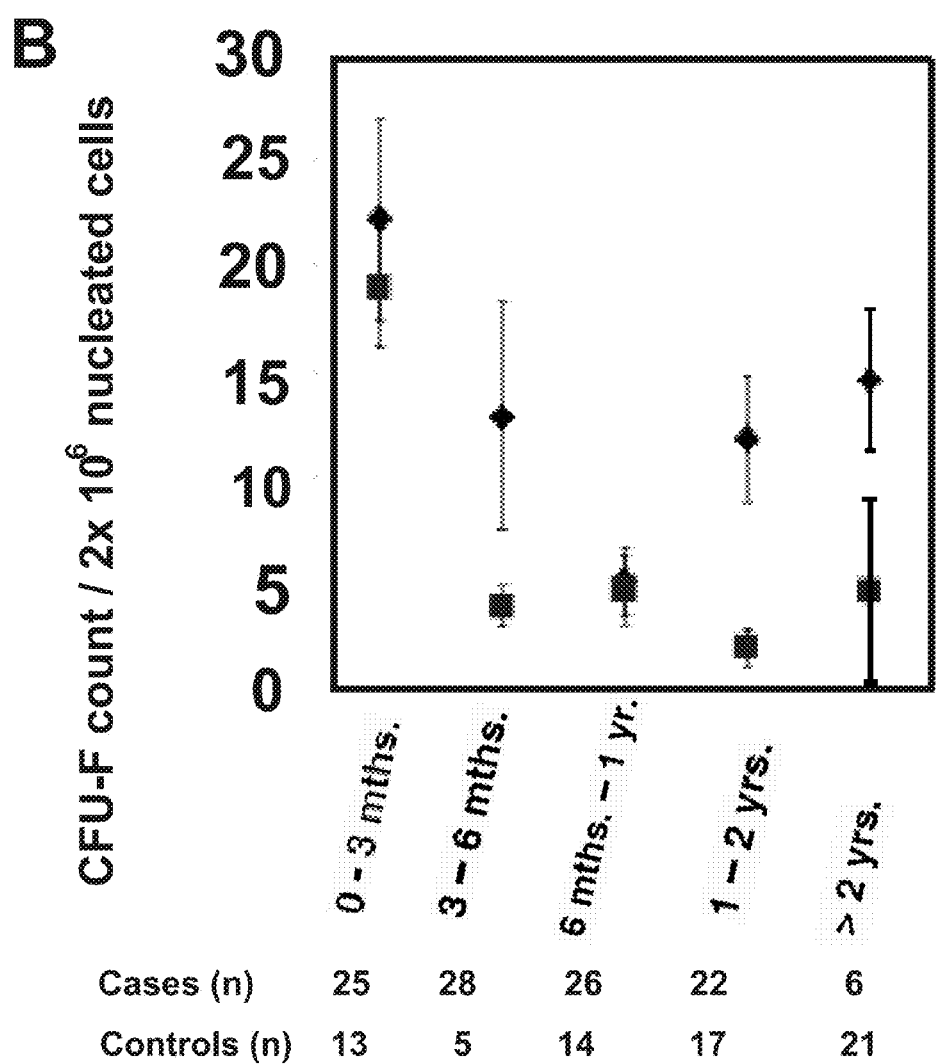

CFU-F counts in the BAL fluid obtained from lung transplant recipients demonstrated significant variability (range from 0 to 60, mean=9.59, SD=12.92). An example of this is shown in FIG. 2A. To determine the factors which modulate the number of LR-MSCs in the BAL, the influence of various clinical variables on the measured number of CFU-Fs from the BAL fluid was analyzed using generalized estimating equations. Time from transplantation to BAL, evidence of acute rejection on biopsy, and BOS-diagnosis by pulmonary function criteria at the time of BAL were found to be important predictors of CFU-F counts as seen in Table 4. Time post-transplant of greater than 90 days was associated with a 0.30 fold lower CFU-F count (95% CI=0.19-0.49; p<0.0001). By histology, the presence of acute rejection on concurrently performed lung biopsies was predictive of higher CFU-Fs in BAL (1.74 fold increase; 95% CI=1.14-2.67; p=0.011). Two cases of organizing pneumonia and one case of proliferative BO were noted in this cohort. High CFU-F counts (50, 47 and 50 CFU-Fs/$2\times10^6$ million cells) were noted in those cases. By pulmonary function criteria, BOS diagnosis at the time of BAL was associated with a 1.96 fold higher CFU-F count than a lack of BOS (95% CI=1.01-3.79; p=0.047). The presence of positive bacterial cultures did not predict CFU-F count (p=0.366). Similarly, evidence of cytomegalovirus (CMV) infection, indication for bronchoscopy, and pre-transplant diagnosis were not predictive of number of CFU-Fs in the BAL.

TABLE 4

Clinical variables influencing the number of lung-resident mesenchymal stem cells (CFU-Fs) in BAL samples in multivariate analysis (N = 177).

| Variable | Estimate[2] (95% CI) | P-value[1] |
|---|---|---|
| Time post-transplant >90 days | 0.30 (0.19-0.49) | <0.0001[+] |
| Presence of acute rejection on biopsy | 1.74 (1.14-1.67) | 0.011[+] |
| Presence of BOS | 1.96 (1.01-3.79) | 0.047[+] |
| Positive bacterial cultures | 1.43 (0.66-3.07) | 0.366 |
| Positive CMV cultures | 0.74 (0.28-1.95) | 0.537 |
| Non surveillance bronchoscopy (vs. surveillance) | 1.02 (0.58-1.82) | 0.938 |
| Pre-transplant Diagnosis | | |
| Idiopathic pulmonary firbrosis | 1.01 (0.62-1.64) | 0.985 |
| Emphysema | 1.06 (0.66-1.73) | 0.803 |
| Others | 1.00[3] | NA[3] |

[1]P-values generated from multivariate generalized estimating equation models accounting for corelation within patients; p-values adjust for all other factors shown.
[2]Estimates indicate the multiplicative increase or decrease in expected CFU-F count according to the factor being true versus false, other factors held constant.
[3]Reference population.
[+]P < 0.05

To study the association of CFU-F count over time by presence and absence of rejection, BAL samples were divided into two cohorts. Cases (n=70) consist of BAL samples from patients with either presence of histological rejection on concurrently performed biopsies or a diagnosis of BOS at the time of or within 6 months of BAL. Controls (n=107) consist of BAL samples with no concurrent evidence of acute rejection or BOS. FIG. 2B demonstrates mean CFU-F count over time in these two cohorts. BAL samples obtained within the first 90 days of transplant demonstrated high CFU-F counts in both cases and controls. CFU-F counts in BAL declined dramatically after 3 months and remained low for the rest of the post-transplant period in the control cohort. In contrast, significantly higher CFU-F counts were noted at later time points post-lung transplantation in the case cohort (Wilcoxon Rank Sum p-values comparing CFU-F counts between cases and controls at 1-2 years and >2 years post lung-transplantation were 0.002 and 0.06 respectively).

The presence of increased numbers of LR-MSCs early post-transplant and in association with histological and physiologic evidence of rejection demonstrates that this endogenous population of MSCs in the lung expands in response to injury.

Increased Numbers of LR-MSCs in BAL Predict BOS Onset

Figure 3A:
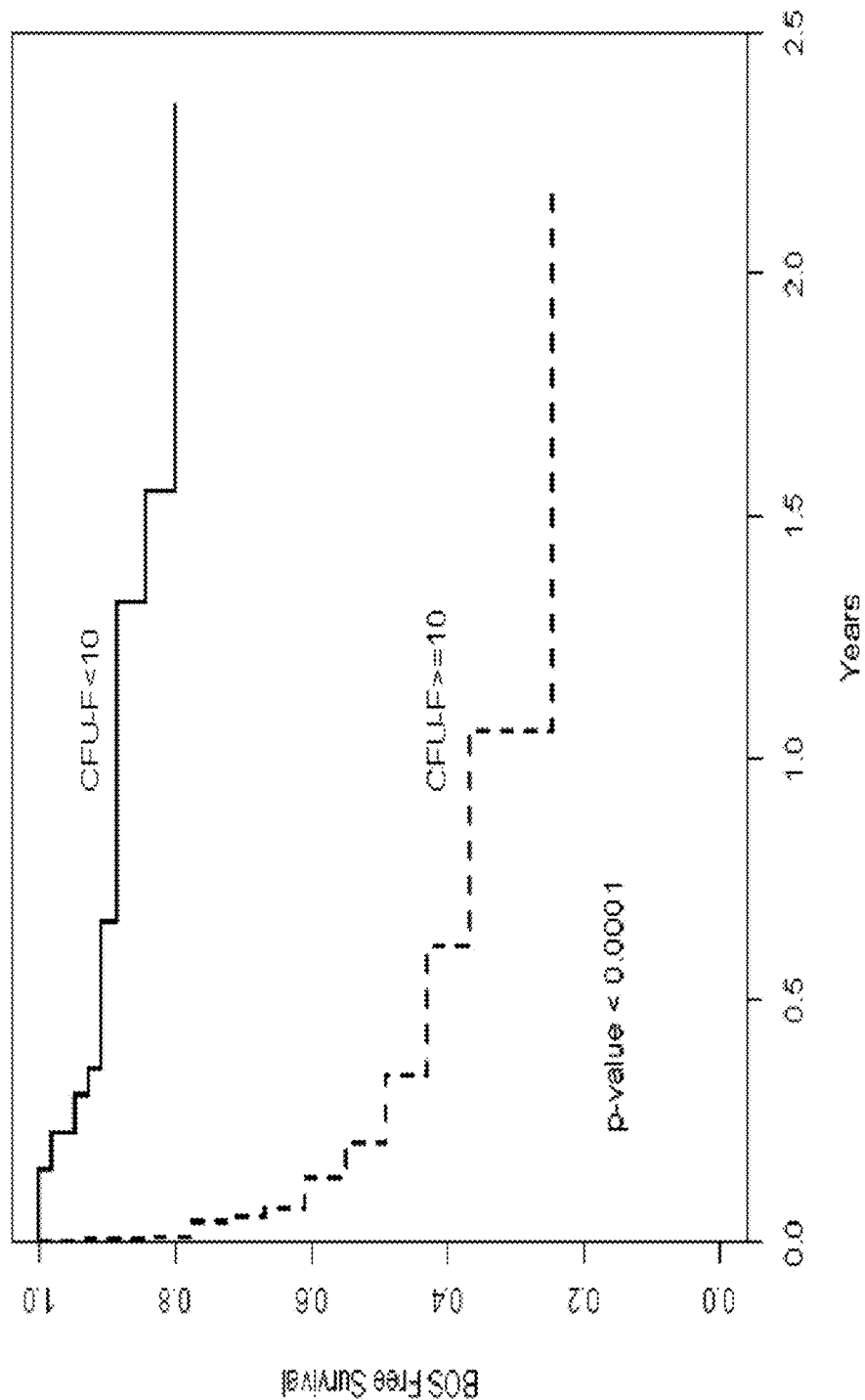
FIG. 3 shows numbers of LR-MSCs in bronchoalveolar lavage fluid as predictors of BOS onset. (A), Kaplan-Meier curve demonstrating time to BOS in lung transplant recipients grouped by number of CFU-Fs in BAL (CFU-F≥10, dashed line; CFU-F<10, solid line). (B), CFU-group specific adjusted time to BOS plots based on survival estimates obtained using hazards estimated with Cox models adjusted for average patient profile. Average covariate profile is as follows: time from transplant to BAL=1.51 years; probability of being female=52.6%; probability of diagnosis of AR on transbronchial biopsies=19.2%; probability of pre-transplant diagnosis of IPF=32.9%, COPD=36.8%; probability of single lung transplantation=50%)
Figure 3B:
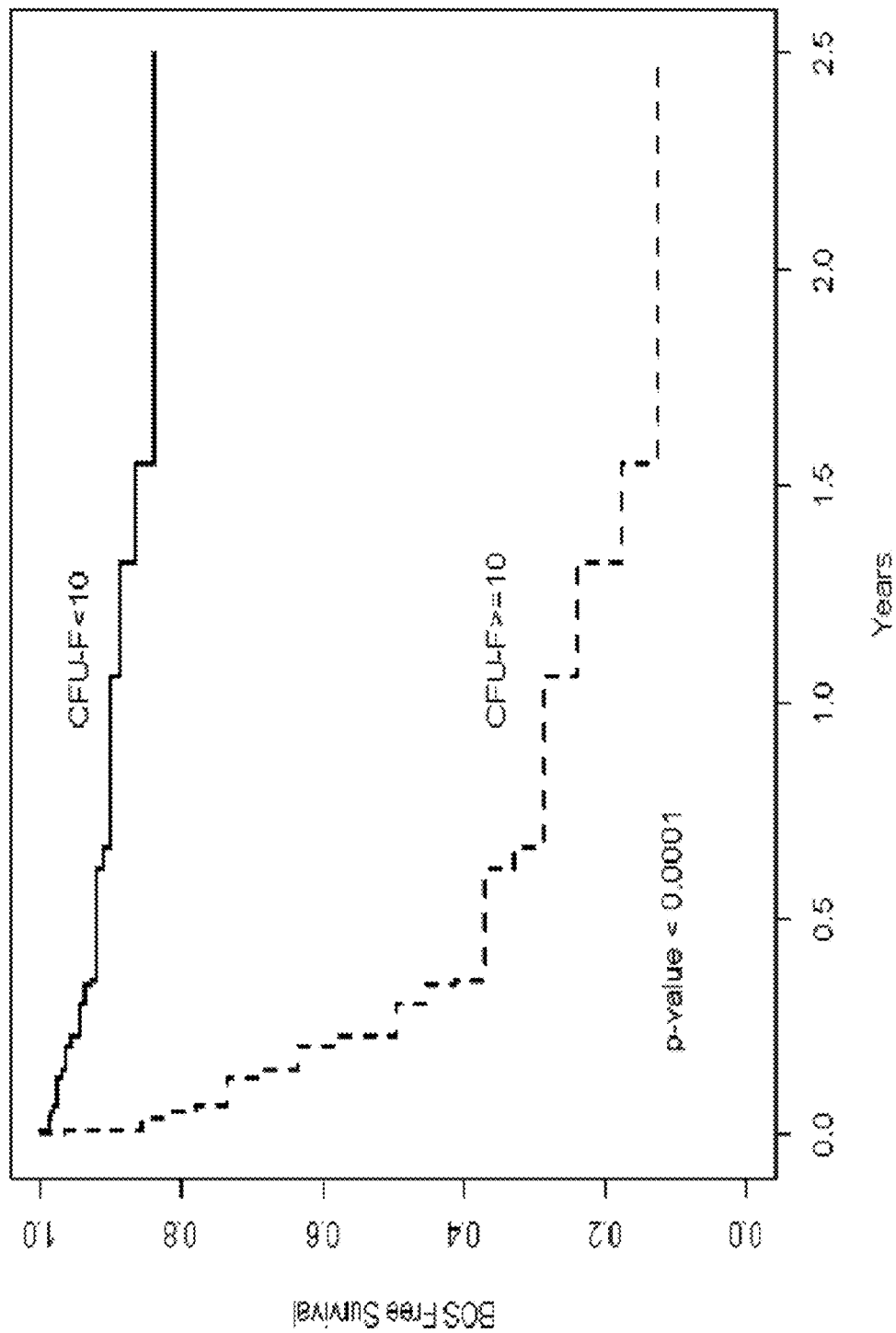

BOS represents a remodeling response of the host to repeated immune and nonimmune-mediated insults that is thought to progress from lymphocyte-mediated cytotoxicity directed at the respiratory epithelium, to fibrosis which obliterates the airway lumen (Estenne et al. (2002) Am. J. Respir. Crit. Care Med. 166:440-444; Hertz et al. (1992) PNAS USA 89:10385-10389; each herein incorporated by reference in its entirety). Data presented herein demonstrating that LR-MSCs increase with evidence of injury indicate that LR-MSC accumulation in airspaces precedes development of BOS and can be used as a biomarker of BOS onset. The ability of the numbers of LR-MSCs to predict future BOS onset was analyzed in BAL samples obtained from BOS-free patients who were greater than 6 months post-lung transplantation. The cohort included 76 BAL samples obtained from 62 patients. For the purpose of data analysis, high CFU-F count was defined as CFU-F≥10 per 2×10$^6$ nucleated cells. This threshold was based on estimated means from parameter estimates obtained from the GEE model shown in Table 4. In univariate analyses, high CFU-F count (CFU-F≥10 in BAL 6 months after transplantation) was found to be a significant predictor of subsequent BOS development (hazard ratio [HR], 8.65; 95% CI, 3.30-22.66; p<0.0001). Kaplan-Meier curves shown in FIG. 3A demonstrate time to BOS in lung transplant recipients grouped by number of CFU-Fs in BAL. Median time to development of BOS from a BAL sample demonstrating CFU-F count≥10 was 75 days; 63% of patients with high CFU-F counts in their BAL developed BOS by 1 year compared to 12% of patients with low CFU-F counts. In multivariate analysis (Table 5), after adjusting for gender, type of transplantation (single vs. bilateral), pre-transplant diagnosis (IPF, emphysema or others), presence or absence of acute rejection, and time post-transplantation, high CFU-F count remained a significant predictor of BOS onset (HR, 11.76; 95% CI, 3.93-35.18; p<0.0001). Cox model-based survival estimates are shown for an average patient profile in FIG. 3B.

TABLE 5

Multivariable proportional-hazards analysis of the risk of BOS onset by variables present at the time of BAL (n = 76).

| Variable | Hazard Ratio | 95% CI (lower) | 95% CI (upper) | P-value |
|---|---|---|---|---|
| CTU-F count ≥10 | 11.76 | 3.93 | 35.18 | <0.0001[+] |
| Time post-transplant (Years) | 0.98 | 0.76 | 1.26 | 0.874 |
| Presence of acute rejection | 1.28 | 0.37 | 4.44 | 0.698 |
| Pre-transplant Diagnosis | | | | |
| Idiopathic Pulmonary Fibrosis | 2.09 | 0.33 | 13.22 | 0.432 |
| Emphysema | 0.97 | 0.09 | 10.84 | 0.979 |
| Others | ref | ref | ref | ref |
| Type of Transplant (Bilateral) | 0.54 | 0.13 | 2.24 | 0.396 |
| Gender (male) | 0.52 | 0.17 | 1.57 | 0.243 |

[+]P < 0.05

Cell count and differential were available on 150 BAL samples. Increased proportions of neutrophils and decreased numbers of macrophages in BAL fluid were associated with increased CFU-F counts (p=0.01 and 0.008 respectively). The proportion of lymphocytes in BAL did not predict LR-MSC CFU-F counts (p=0.81). As neutrophils in BAL have been previously associated with development of BOS (DiGiovine et al. (1996) J. Immunol. 157:4194-4202; herein incorporated by reference in its entirety), the relationship between neutrophils and various clinical variables was further investigated. Similar to CFU-F counts, presence of acute rejection and BOS was associated with higher neutrophil numbers in BAL (p=0.014 and 0.023 respectively). However, while bacterial cultures did not predict CFU-F counts, positive bacterial culture was strongly associated with higher number of neutrophils in the BAL (p=0.0006). Evidence of CMV in BAL negatively correlated with neutrophil counts (p=0.0064). Of 150 samples with neutrophil counts available, 61 BAL samples from 53 patients were obtained greater than 6 months after transplantation and in the absence of BOS. In this cohort, after adjusting for presence of other clinical variables (AR, gender, type of transplantation (single vs. bilateral), pre-transplant (pre-Tx) diagnosis (IPF, emphysema or others), and time post-transplantation, high CFU count emerged as a much stronger predictor of BOS onset (HR, 9.13; 95% CI, 2.60-31.98; p=0.0005) than neutrophil count (HR, 1.02; 95% CI, 1.00-1.03; p=0.05).

These data demonstrate that increased levels of LR-MSCs or biomarkers thereof in BAL are a potent predictor of future BOS onset.

Figure 4:
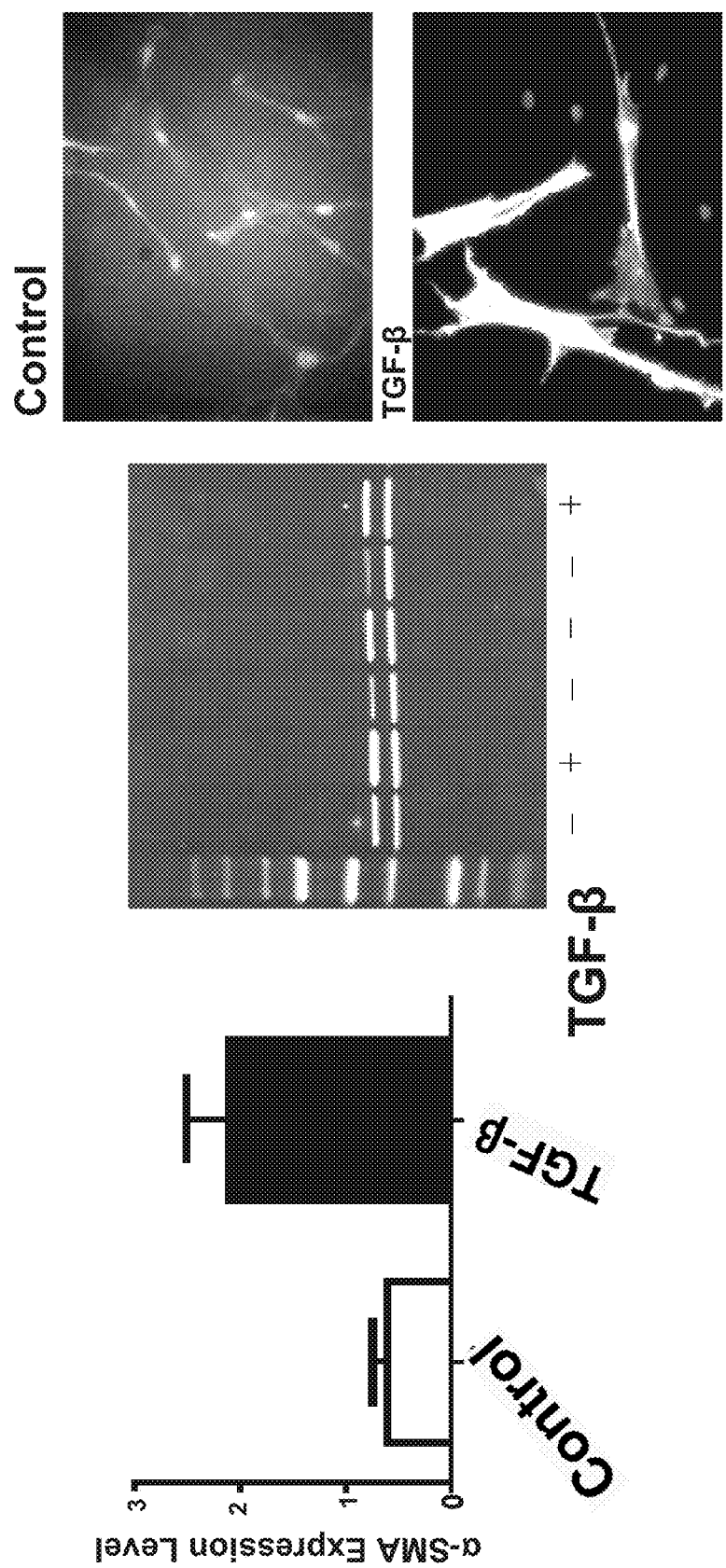
FIG. 4 shows that TGF-β induces differentiation of LR-MSCs to myofibroblast. LR-MSCs were treated with TGF-β (2 mg/ml) and expression of α-SMA protein expression (a marker of myofibroblast differentiation) was studied by western blot and immunocytofluorescence. Left panel demonstrates quantification of α-SMA by densitometry (n=12). Immunoblot for α-SMA (upper band) and GAPDH loading control (lower band) for 3 separate LR-MSC lines in presence and absence of TGF-β is shown in the center panel. Right panel demonstrates α-SMA stress fiber formation in response to TGF-β by immunofluorescence staining

Fibrotic Differentiation Potential of LR-MSCs and Expression of FOXF1 in Myofibroblasts in Human Lung Transplant Biopsies While the present invention is not limited to any particular mechanism, and an understanding of the mechanism is not necessary to practice the present invention, it is contemplated that the increased presence of LR-MSCs in the presence of BOS and the demonstration that this increase precedes BOS onset indicates that LR-MSCs plays a role in the pathogenesis of BO. A mesenchymal cell which has been shown to be a key effector cell in fibrotic processes is the myofibroblast, identified by its expression of intracellular contractile protein α-smooth muscle actin (α-SMA). Lung biopsies of patients with BO demonstrate infiltration by myofibroblasts (Lama et al. (2006) Am. J. Pathol. 169:47-60; herein incorporated by reference in its entirety). To determine whether LR-MSCs can differentiate into myofibroblasts, LR-MSCs were exposed to pro-fibrotic mediator transforming growth factor-β (TGF-β) (2 ng/ml). Treatment with TGF-β led to a significant increase in LR-MSC α-SMA expression, both by western blot and immunofluorescent staining, demonstrating the ability of LR-MSCs to differentiate into myofibroblasts in a pro-fibrotic milieu (FIG. 4).

Figure 5:
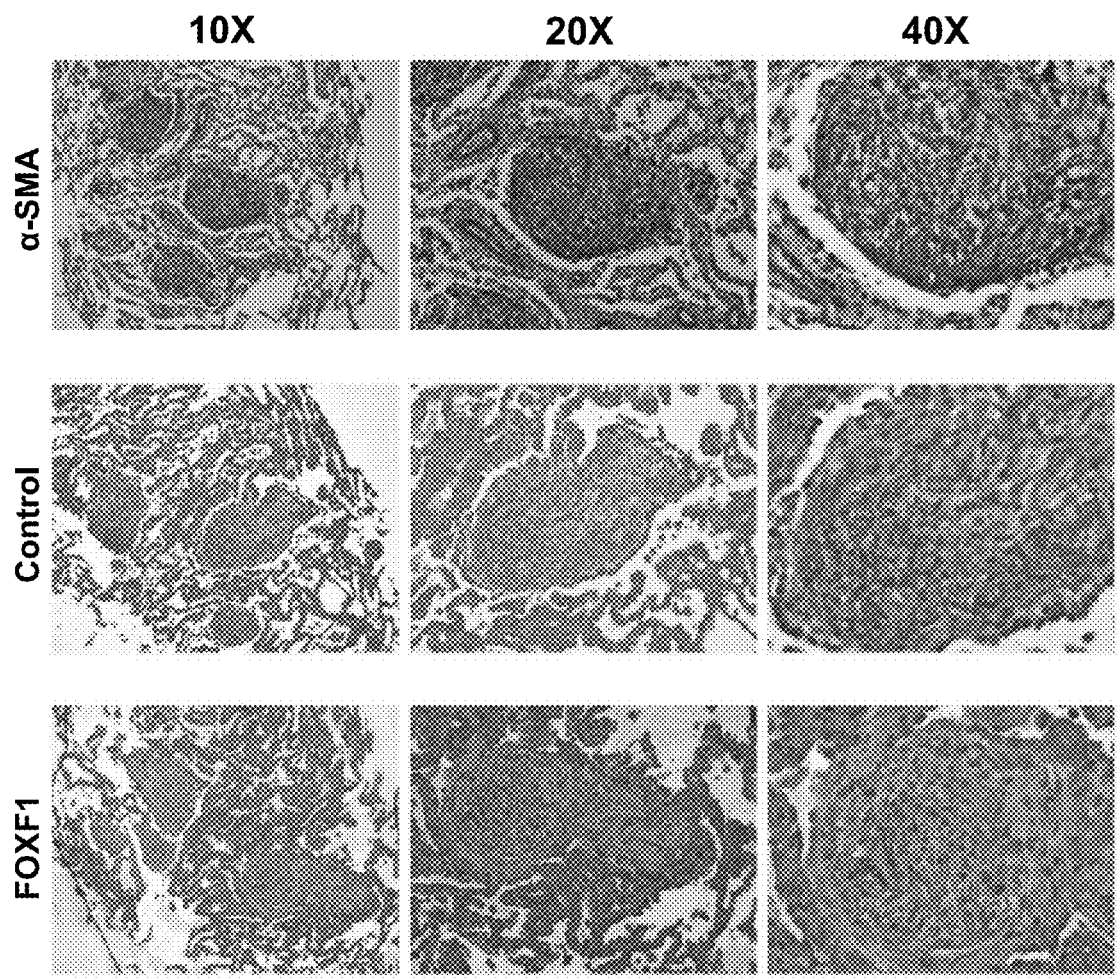
FIG. 5 shows FOXF1 expression in myofibroblasts present in fibrotic lesions in human lung allografts. Representative sections of transbronchial lung biopsy are shown, demonstrating organizing pneumonia in a lung transplant recipient, stained for α-SMA (by immunohistochemical staining) and FOXF1 (by in situ hybridization). Spindle shaped cells within the fibrotic lesion demonstrate α-SMA staining (top panels) signifying presence of myofibroblasts. FOXF1 mRNA expression was detected by in situ hybridization in the myofibroblasts (bottom panel). Controls (center panel) were performed using DIG-labeled control mRNA.

To determine whether myofibroblasts seen in the fibrotic lesions of lung allograft could be derived from LR-MSCs, additional analyses were performed. As FOXF1 was shown to be differentially expressed in LR-MSCs compared to BM-MSCs, the expression of FOXF1 in lung transplant biopsies was studied. Biopsies demonstrating evidence of either bronchiolitis obliterans or organizing pneumonia were analyzed for expression of FOXF1 and α-SMA. As shown in FIG. 5, intensely positive α-SMA staining myofibroblasts were identified in the fibrotic lesions. These cells were also found to express FOXF1 by in situ hybridization. The fibrotic differentiation of LR-MSCs in response to pro-fibrotic stimuli and the expression of FOXF1 in fibrotic lesions in human lung transplant biopsies indicate endogenous LR-MSCs as a source of myofibroblasts.

Example 2

Resident Tissue-Specific Mesenchymal Progenitor Cells Contribute to Fibrogenesis in Human Lung Allografts In this Example, the role of LR-MSCs in post-lung transplant fibrogenesis was investigated, and FOXF1 was analyzed as a surrogate marker for LR-MSCs in cells from bronchoalveolar lavage (BAL) samples.

Methods

Isolation of Lung-Derived MSCs and Other Cell Lines

Figure 9:
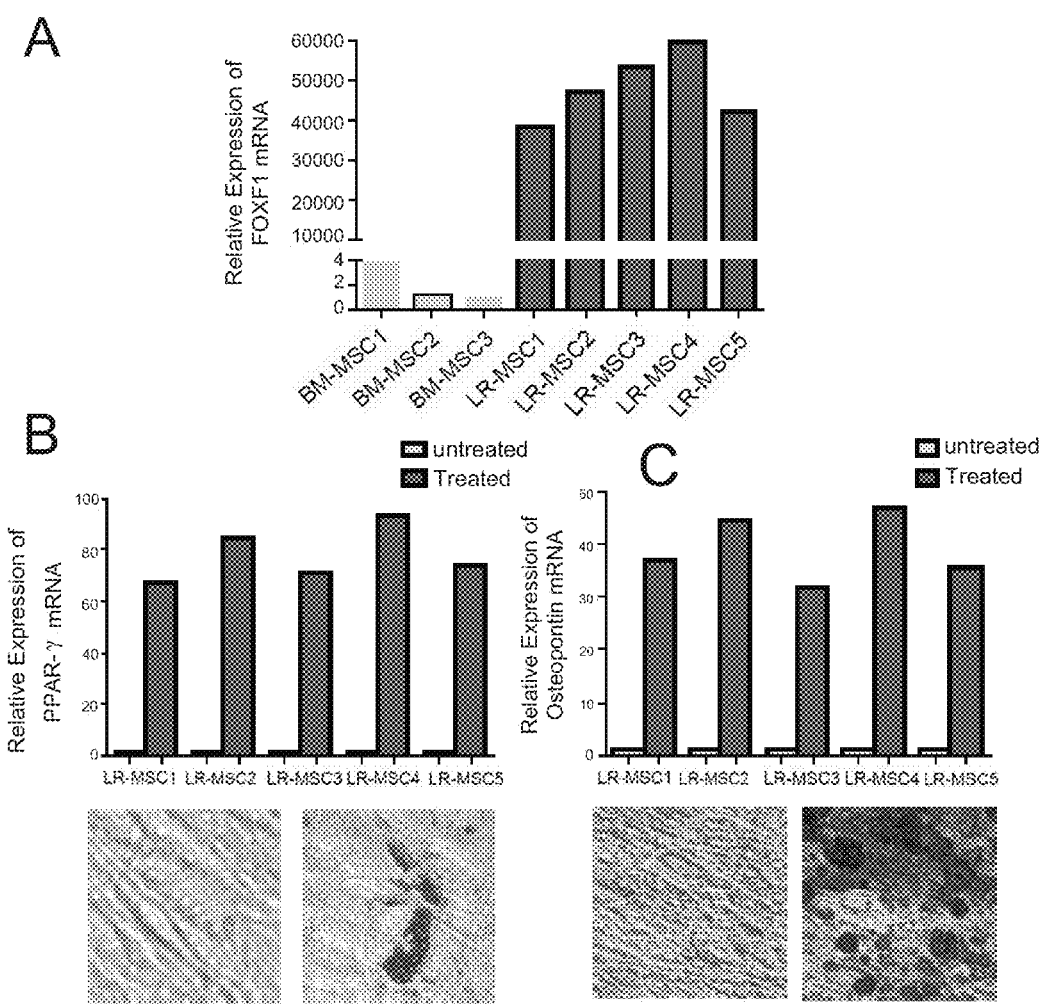
FIG. 9 shows the characterization of LR-MSCs from BAL fluid of human lung allografts. Immunophenotypic analysis, multilineage differentiation potential and FOXF1 expression of mesenchymal cells isolated from bronchoalveolar lavage fluid of 5 separate lung transplant recipients is shown. Panel (A), Mesenchymal cells isolated from BAL fluid of lung transplant recipients were expanded in culture and immunostained for cell-surface markers with specific mAbs. % of positive cells relative to the total number of cells analyzed as analyzed by flow cytometry is shown. These cells were predominantly positive for CD73, CD90, CD105, and CD44 and uniformly negative for the hematopoietic lineage markers CD45. Panel (B), Same cell lines were investigated for their in vitro multilineage differentiation capacity by culturing them in either control or differentiation-inducing conditions. Real time PCR was performed to analyze the expression of mRNAs specifically related to adipogenic, and osteogenic activity under inductive culture conditions. Expression of PPARγ (indicative of adipogenic activity), and osteopontin (indicative of osteogenic activity) was upregulated in all 5 cell lines. Accumulation of lipid droplets (indicating adipocytic differentiation) was demonstrated by staining with oil red-O in treated cells. Osteocytic differentiation was indicated by calcium deposition as demonstrated by alizarin red staining in treated cells. No staining was observed in control untreated cells. Panel (C), mRNA expression of FOXF1 by real time PCR in the same 5 cell lines is shown compared to 3 separate bone-marrow derived MSC lines.
Figure 10:
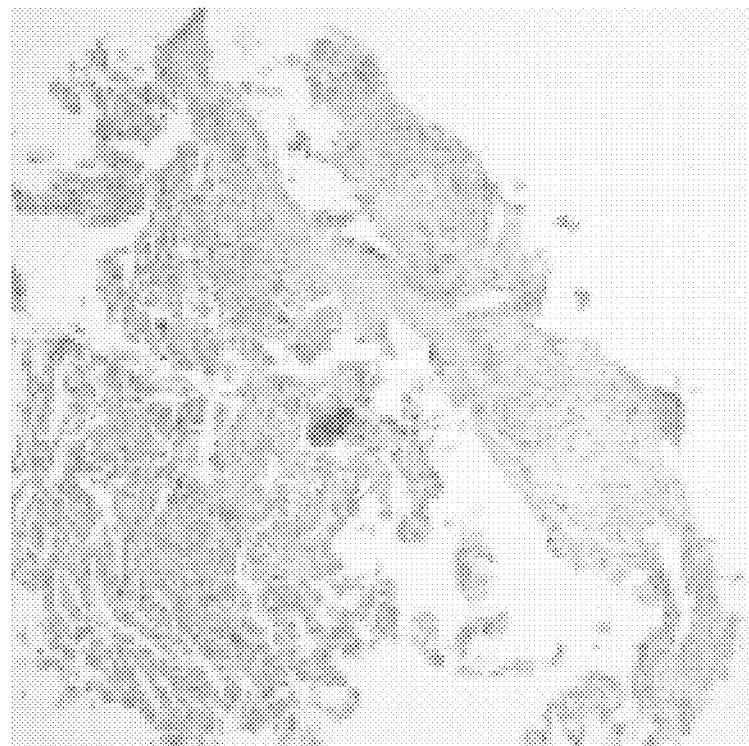
FIG. 10 shows α-SMA staining of human lung biopsies. Staining with α-SMA was performed according to standard clinical laboratory procedure. Negative control for α-SMA staining is presented on the right. Magnification ×100
Figure 10:
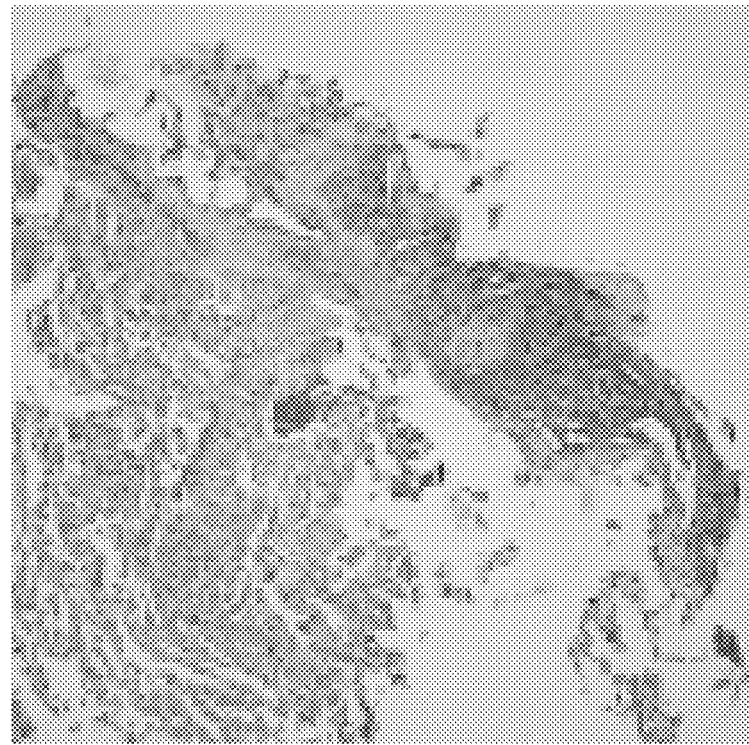

Mesenchymal stromal cells were derived from BAL of lung transplant recipients by plastic adherence and subsequent expansion of CFU-Fs as previously described (Example 1). Surface marker expression for cells utilized in experiments described herein was determined using flow cytometry. LR-MSCs were negative for CD45 and positive for CD73, CD105, CD90 and CD44. Furthermore, their multilineage differentiation potential was confirmed by inducing differentiation into osteocytes and adipocytes (FIG. 9). Cells were maintained in culture in DMEM with penicillin/streptomycin and 10% FCS at 37° C. in 5% $CO_2$ and used at passages 2-6. LR-MSCs obtained from individual BAL samples were treated as separate cell lines. BOS was defined by physiological testing according to the International Society of Heart and Lung Transplantation guidelines (Estenne et al. (2002) J. Heart Lung Transpl. 21:297-310; herein incorporated by reference in its entirety). Bone marrow derived MSCs (BM-MSCs) were isolated from normal human bone marrow aspirates (Lama et al. (2007) J. Clin. Invest. 117:989-996; herein incorporated by reference in its entirety). Alveolar epithelial cells (A549) and human pulmonary artery endothelial cells (HPAEC) were purchased from American Type Culture Collection (Manassas, Va.) and Lonza (Walkersville, Md.) respectively. Primary airway epithelial cells were isolated from healthy donors and cultured in bronchial epithelial cell growth medium (Lonza) (Sajjan et al. (2004) Infect. Immun. 72:4188-4199; Schneider et al. (2010) J. Respir. Crit. Care Med. 182:332-340; each herein incorporated by reference in its entirety).

Affymetrix and Real-Time Quantitative PCR Analysis

Total RNA was prepared using the RNeasy mini kit (Qiagen, Inc. Valencia, Calif.) as per manufacturer's instructions. Realtime quantitative PCR analysis was performed on an ABI Prism 7000 SDS (Applied Biosystems, Foster City, Calif.) using TaqMan PCR Master Mix (Applied Biosystems). The TaqMan real time PCR primers included Hs00230962_m1 for FOXF1, Hs00430330_m1 for HOXA5, and Hs00357820_m1 for HOXB5 (Applied Biosystems). Affymetrix array hybridization and scanning were performed by the UMCCC Affymetrix and cDNA Microarray Core Facility, University of Michigan, Ann Arbor, Mich., USA, using Human U133 plus 2.0 chips. Expression value for each gene was calculated using a robust multiarray average and are stored as $log_2$ transformed data.

Immunofluorescence Microscopy and Western Blot Analysis

Immunofluorescence staining for α-smooth muscle actin (α-SMA) and IL-13 receptor α1 (IL-13Rα1) was performed on LR-MSCs plated at a density of 50,000 cells per 35-mm cell culture dish using mouse monoclonal anti-α-SMA (clone 1A4, Dako, Carpenteria, Calif.) and anti-IL-13Rα1 antibodies (R&D, Minneapolis, Minn.). Western blot for α-SMA and Collagen I was performed (Lama et al. (2006) Am. J. Pathol. 169:47-60; Huang et al. (2007) Am J. Physiol. Lung Cell Mol. Physiol. 292:L405-413; each herein incorporated by reference in its entirety), using monoclonal α-SMA (clone 1A4, Dako, Carpinteria, Calif.) at 1:1,000 dilution and rabbit polyclonal antibody to Collagen I (Cedarlane Laboratories, Ontario, Canada) at 1:500 dilution.

Immunohistochemical Staining and In Situ Hybridization

Paraffin-embedded sections from biopsies demonstrating organizing pneumonia or bronchiolitis obliterans were obtained under an IRB-approved protocol. Staining with α-SMA was performed according to standard clinical laboratory procedure as previously described (Lama et al. (2006) Am. J. Pathol. 169:47-60; herein incorporated by reference in its entirety). Human FOXF1 ORFeome Collaboration Clone (I.D.1000-67187, Accession # EU832158) was purchased from Open Biosystems (Huntsville, Ala.). Plasmid DNA was purified using a Qiagen maxi prep kit (Valencia, Calif.) and amplified by polymerase chain reaction using human FOXF1 primers containing EcoR1 and Hind III cutting sites (forward and reverse respectively) from Integrated DNA Technologies (Coralville, Iowa) as previously described (Example 1) (forward primer: 5' ATG GAA TTC GCG TCG TCC GGC CCG T 3' (SEQ ID NO:1); reverse primer: 5' GGG CCA AGC TTT CCA CGT TGC CCG G 3' (SEQ ID NO:2)). Purified DNA was linearized, and denatured to generate single stranded DNA. Single stranded DNA was then labeled with digoxigenin (DIG) according to the manufacturer's protocol using DIG RNA labeling kit (SP6/T7) from Roche Applied Science (Penzberg, Germany). In situ hybridization was performed according to the manufacturer's protocol using a kit purchased from Biochain Institute Inc. (Hayward, Calif.). Sections were digested with (20 µg/ml) proteinase K (Invitrogen, Carlsbad, Calif.) and color was developed using Fast Red TR/Napthol AS-MX (Sigma, Saint Louis, Mo.). To demonstrate co-localization of α-SMA and FOXF1, antigen retrieval was performed on paraffin embedded sections, followed by FOXF1 (1:25 dilution, Sigma-Aldrich, St. Louis, Mo.) and α-SMA (1:1000, DAKO, Carpinteria, Calif.) staining utilizing ABC Elite kit according to manufacturer's protocol (Vector labs, Burlingame, Calif.). Tyramide signal amplification (TSA) system from Perkin Elmer (Covina, Calif.) was used to develop the final stain.

In Vitro Epithelial Mesenchymal Transformation (EMT)

Human lung epithelial cells (A549) were stimulated with TGF-β (5 ng/ml) and harvested at 0, 0.5, 1, 2, 4, 8, 16, 24, and 72 hours after treatment (Keshamouni et al. (2009) J. Proteome Res. 8:35-47; herein incorporated by reference in its entirety). Total RNA was prepared from three biological replicates of each condition and RNA transcripts were assayed using Affymetrix HG-U133 plus_2.0 chip array. Two-way ANOVA models with effects for 3 experiments and 9 time points were fit to the data for each probe-set.

Statistics

Students t-tests were used to determine P values when comparing two groups. When comparing three or more groups, analysis of variance was performed with a posthoc Bonferroni test to determine which groups showed significant differences.

Results

Figure 6A:
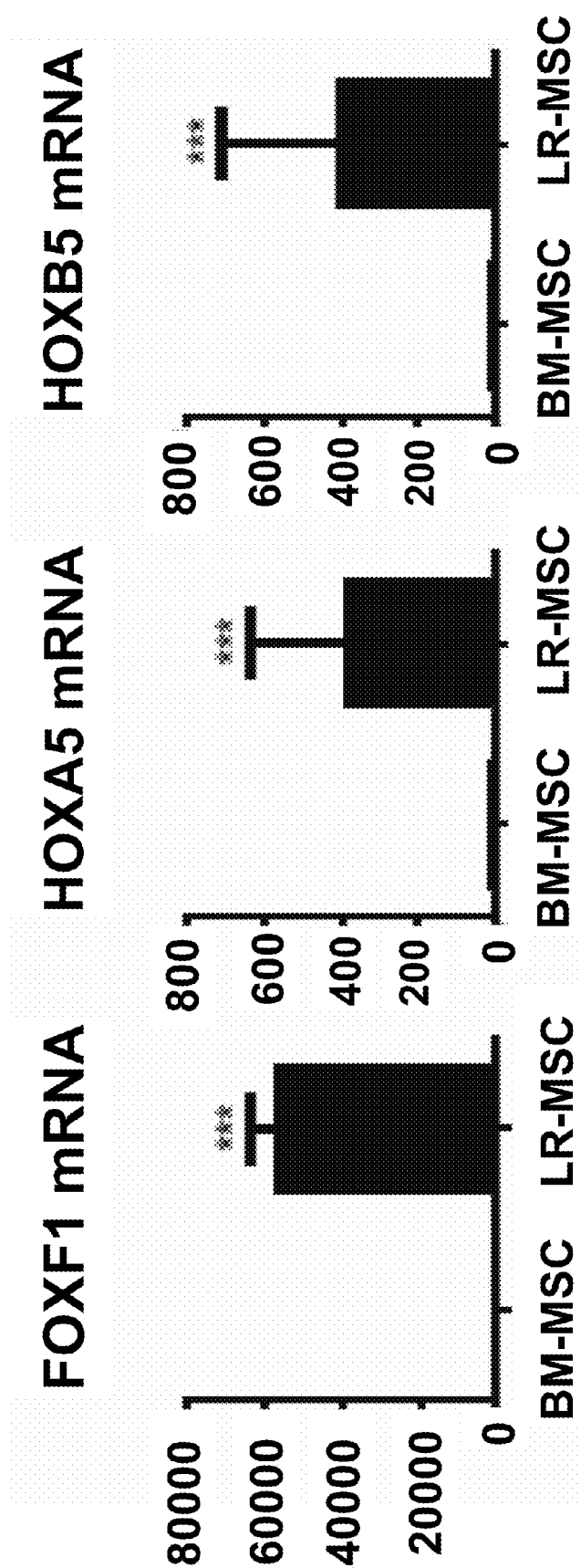
FIG. 6 shows expression patterns and TGF-β-induced myofibroblast differentiation potential and expression of embryonic lung mesenchyme-associated transcription factors in lung-derived MSCs. Panel (A), Increased expression of embryonic lung mesenchyme associated transcription factors in lung-derived MSCs. mRNA expression of FOXF1, HOXA5 and HOXB5 in LR-MSCs isolated from bronchoalveolar lavage fluid of lung allografts (n=10 LR-MSC lines derived from individual patients) was compared to bone marrow-derived MSCs (BM-MSCs, n=3) by real-time PCR. * P<0.0001. Panels (B) and (C), LR-MSCs demonstrate myofibroblast differentiation potential in response to the pro-fibrotic mediator TGF-β. LR-MSCs isolated from normal lung allografts, without evidence of acute or chronic rejection, were treated with or without TGF-β1 (2 ng/mL) for 24 hours. (B): Immunofluorescence staining of LR-MSCs demonstrated an increase in α-SMA positive stress fibers in response to TGF-β1. A quantitative analysis of α-SMA positive cells across 10 high power fields in three normal cell lines is shown in the panel on the right. * p<0.0001 C: Effect of TGF-β on α-SMA and Collagen I protein expression, analyzed by western blot analysis. Immunoblots shown are from a representative experiment, with graphical data representing the densitometric ratio of the protein of interest to loading control proteins. Data represent the mean±SEM of experiments with LR-MSCs derived from 10 lung transplant recipients. * p=0.0002;  p=0.006

Human Lung Allograft-Derived MSCs Demonstrate Expression of Lung Embryonic Mesenchymal Factors To investigate whether lung allograft-derived MSCs represent a tissue specific resident mesenchymal cell population, the gene expression profile of mesenchymal transcription factors in LR-MSCs was studied and compared to that of BM-MSCs as described in Example 1 (see Table 2). Real-time PCR analysis confirmed increased expression of FOXF1, HOXA5 and HOXB5 in LR-MSCs compared to BM-MSCs (FIG. 6A). In experiments described herein, a 35,000-fold greater expression of FOXF1 was seen in LR-MSCs than in BM-MSCs (p<0.0001). Furthermore, a 100-fold increased expression of HOXA5 (p<0.0001) and a 150-fold increased expression of HOXB5 (p<0.0001) were noted in LR-MSCs compared to BM-MSCs. The FOXF1 mRNA expression by real time PCR, cell surface marker expression by flow cytometry and osteogenic and adipogenic differentiation assay of cells derived from 5 individual patients is presented in the FIG. 9. This unique expression of fetal lung mesenchyme-associated transcription factors in multi-potent MSCs derived from human adult lung shows that LR-MSCs are derived from embryonic mesenchyme and represent a locally resident tissue-specific progenitor cell.

Figure 6B:
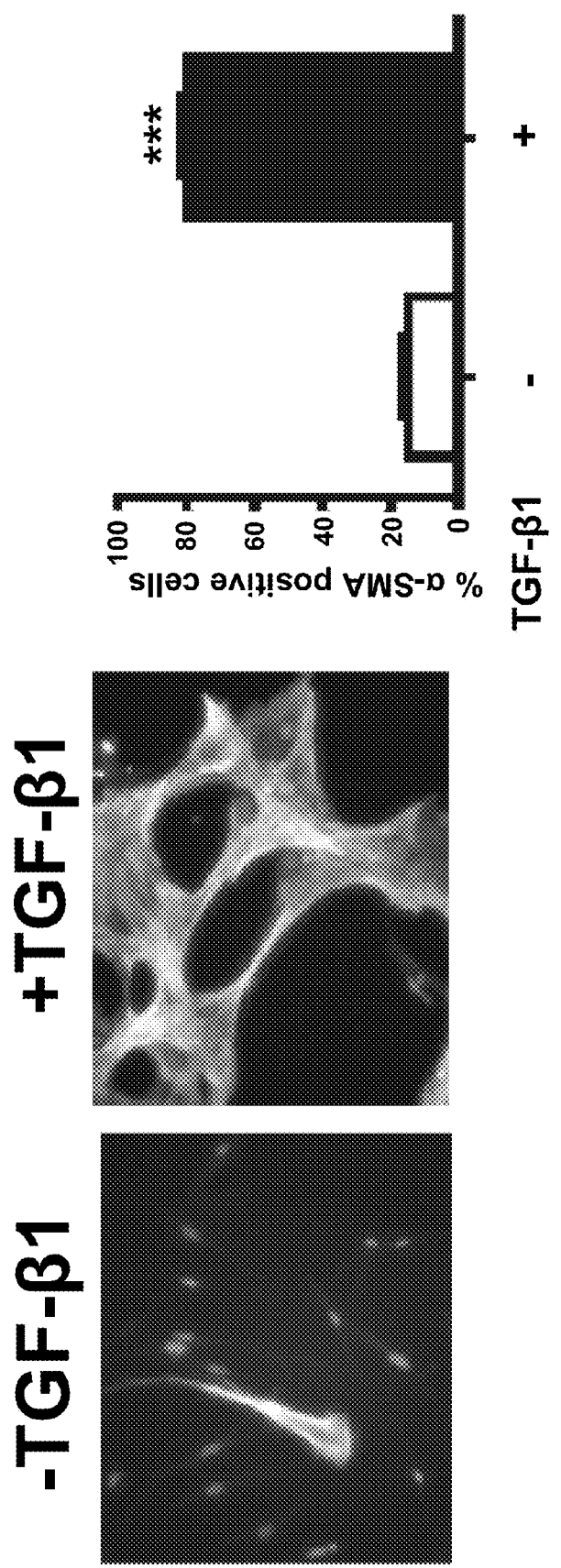
Figure 6C:
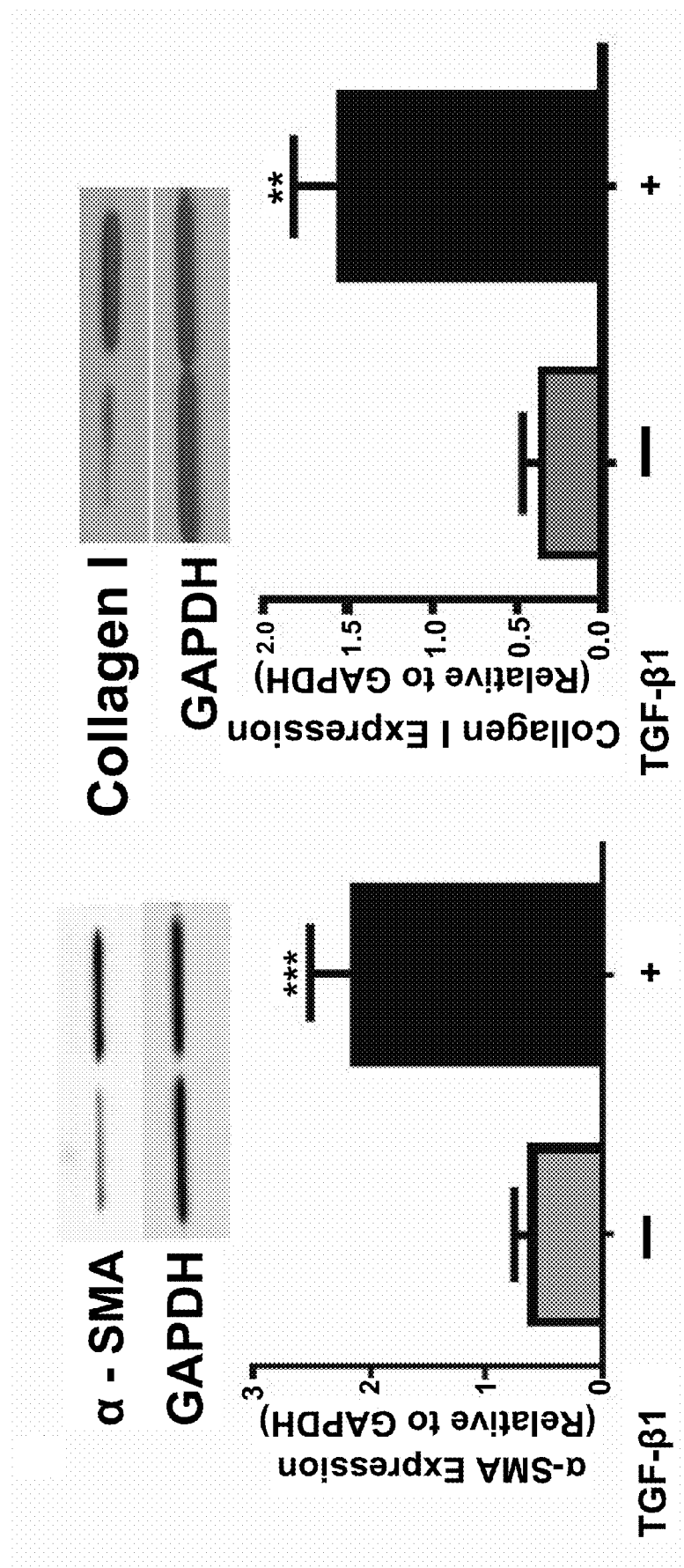
Figure 7:
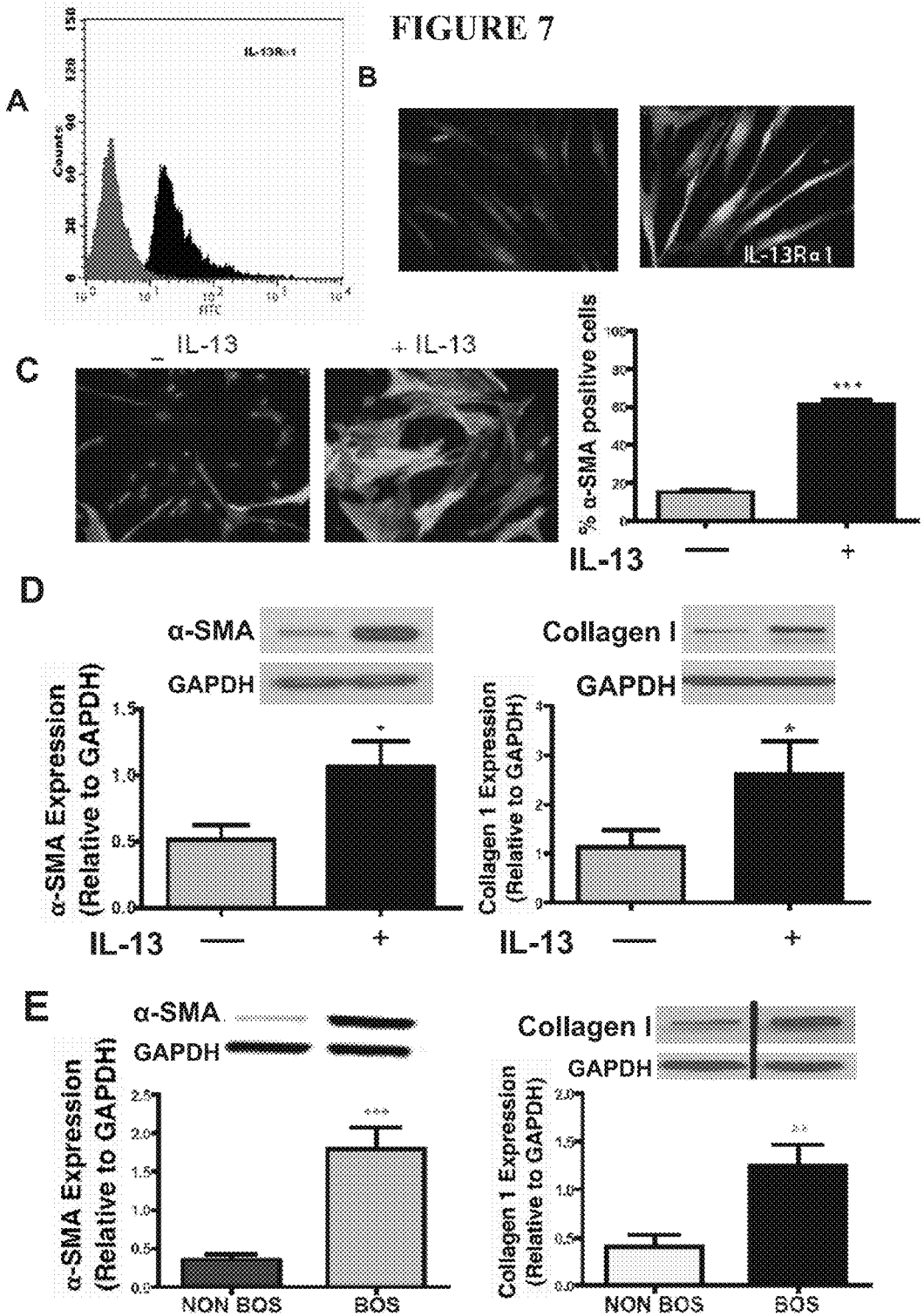
FIG. 7 shows expression of IL-13 receptor in LR-MSCs and pro-fibrotic differentiation in response to IL-13. Panels (A) and (B): LR-MSCs demonstrate expression of IL-13 receptor α1. (A), Immunophenotyping by flow cytometric analysis demonstrates positive IL-13 receptor α1 expression on LR-MSCs isolated from human lung allografts. The histogram shows IL-13Rα1 staining in black and isotype control staining in shown in grey (n=5). (B), Immunofluorescent staining of LR-MSCs demonstrates IL-13Rα1 positive staining (compared to control unstained). Panels (C) and (D): LR-MSCs demonstrate pro-fibrotic differentiation in response to IL-13. LR-MSCs isolated from normal lung allografts, without evidence of acute or chronic rejection, were treated with or without IL-13 (10 ng/mL) for 24 hour. (C), Expression of α-SMA in LR-MSCs±IL-13 is shown utilizing immunofluorescent staining A quantitative analysis of α-SMA positive cells across 10 high power fields in three normal cell lines is shown in the panel on the right. *** p<0.0001 (D), Effect of IL-13 on α-SMA and Collagen I protein expression, analyzed by western blot analysis. Data represent the mean±SEM of experiments with LR-MSCs derived from 10 lung transplant recipients. * p<0.05 E, LR-MSCs isolated from patients with BOS demonstrate a pro-fibrotic phenotype. α-SMA and Collagen I protein expression in LR-MSCs isolated from patients with and without BOS was compared by western blot analysis. Data represent the mean±SEM of experiments with LR-MSCs derived from 10 lung transplant recipients in each group. * p<0.0001;  p=0.003

LR-MSCs Isolated from Normal Human Lung-Allografts Demonstrate Myofibroblast Differentiation in Response to Pro-Fibrotic Mediators The myofibroblast, the pivotal effector cell of fibrogenic processes, is a differentiated mesenchymal cell marked by expression of the contractile protein α-SMA and a concomitant increased ability to secrete collagen (Hinz et al. (2007) Am. J. Pathol. 170:1807-1816; herein incorporated by reference in its entirety). The availability of MSCs isolated from BAL of human lung allografts provided an opportunity to investigate whether these resident mesenchymal components of the allograft milieu can undergo pro-fibrotic differentiation by cytokines and mediators thought to be associated with BOS. LR-MSCs isolated from BAL of normal lung allografts were exposed to transforming growth factor-β (TGF-β), a pro-fibrotic mediator implicated in BOS pathogenesis (Elssner et al. (2000) Transplantation 70:362-367; Ramirez et al. (2004) Am. J. Pathol. 165:1223-1232; each herein incorporated by reference in its entirety). 79.31±2.81% of the LR-MSCs exposed to TGF-β1 (2 ng/ml) demonstrated α-SMA expression by immunofluorescence compared to 15.09±1.18% α-SMA positive cells noted at baseline (p<0.0001; FIG. 6B). An upregulation of α-SMA protein expression in LR-MSCs treated with TGF-β1 as compared to controls was also observed by western blot analysis (p=0.0002, FIG. 6C). Similarly, Collagen I protein expression demonstrated a significant increase over baseline in LR-MSCs treated with TGF-β1 (p=0.006, FIG. 6C). The pro-fibrotic Th2 cytokine interleukin-13 (IL-13) is critical in the development of luminal obliteration in animal models of BO (Lama et al. (2006) Am. J. Pathol. 169:47-60; Keane et al. (2007) J. Immunol. 178:511-519; each herein incorporated by reference in its entirety), and increased levels of IL-13 are present in BAL of human lung transplant recipients with BOS (Keane et al. (2007) J. Immunol. 178:511-519; herein incorporated by reference in its entirety). Myofibroblasts in human BO lesions express IL-13 receptor α1, the receptor chain necessary for signaling by IL-13 (Lama et al. (2006) Am. J. Pathol. 169:47-60; herein incorporated by reference in its entirety). LR-MSCs demonstrated significant expression of this receptor by both flow cytometry and immunofluorescence microscopy (FIGS. 7A and 7B). Myofibroblast differentiation marked by α-SMA positive stress fiber organization was observed in 60.84+2.73% of cells in response to IL-13 by immunofluorescence (p<0.0001; FIG. 7C). Immunoblot analysis demonstrated increased expression of both α-SMA and collagen I protein in LR-MSCs treated with IL-13 as compared to untreated controls (p=0.016 and 0.034 respectively, FIG. 7D). Together, these data demonstrate that pro-fibrotic factors implicated in BOS can drive LR-MSCs to differentiate into myofibroblasts with a robust capacity to elaborate extracellular matrix proteins important in scar formation.

LR-MSCs Derived from Patients with BOS Demonstrate a Pro-Fibrotic Phenotype Marked by Increased α-SMA Expression and Collagen Secretion The ability of LR-MSCs to undergo fibrotic differentiation in response to pro-fibrotic stimuli prompted investigation into whether BOS is associated with an altered LR-MSC phenotype. Constitutive α-SMA and collagen expression were compared in untreated LR-MSCs obtained from allografts of patients with and without physiologic evidence of BOS. Significantly increased α-SMA expression was seen in patients with clinical evidence of BOS compared to time-matched BOS-free control patients (p<0.0001, FIG. 7E). Examination of α-SMA expression over serial passages demonstrated stable α-SMA expression in control and BOS LR-MSCs.

LR-MSCs isolated from patients with BOS also demonstrated increased baseline collagen I expression (p=0.003, FIG. 7E). Increased collagen synthetic function and α-SMA expression in LR-MSCs isolated from BAL fluid of transplant recipients with BOS show that LR-MSCs have a pathogenic role in the fibroproliferative response culminating in BOS. To determine if MSCs isolated from patients with BOS were also lung rather than bone marrow in origin, FOXF1 mRNA expression was assessed in cells isolated from patients with and without BOS. No difference was noted in the expression of FOXF1 in cells from patients±BOS (p=0.31).

FOXF1 Expression in BAL Correlates with Number of LR-MSCs

Figure 8:
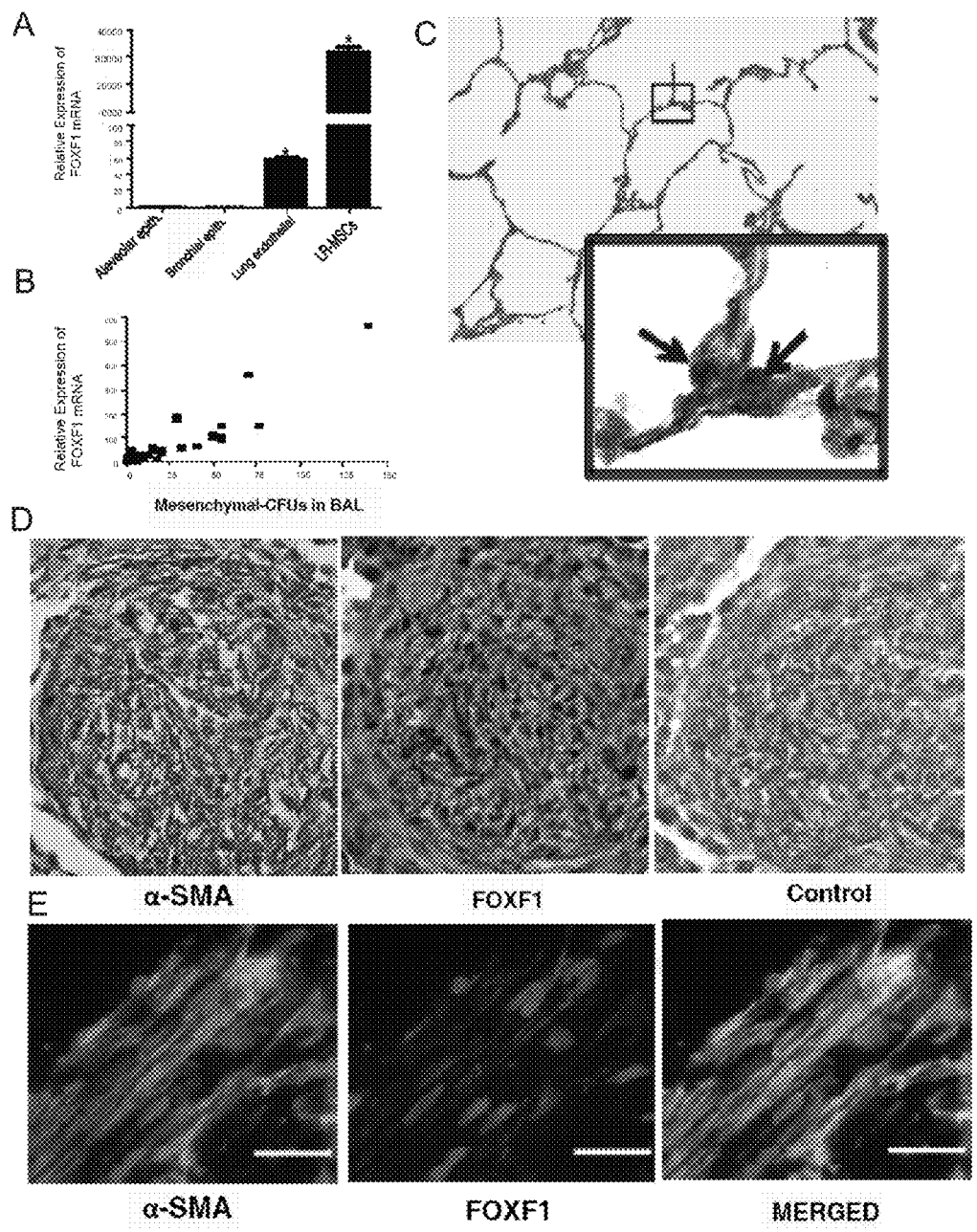
FIG. 8 shows FOXF1 expression in lung tissue, cells from bronchoalveolar lavage cells, and co-expression of FOXF1 and α-SMA in fibrotic lesions. Panel (A). FOXF1 expression in other endogenous lung cellular populations. FOXF1 mRNA expression in human lung allograft-derived MSCs (LR-MSCs), human alveolar epithelial (A549), human lung primary airway epithelial, and human pulmonary artery endothelial(HPAECs) cells by real-time quantitative PCR is shown. Panel (B). FOXF1 mRNA expression in BAL correlates with number of LR-MSCs in human lung transplant recipients. FOXF1 expression in 1×10$^6$ nucleated BAL cells was studied by real time PCR. Numbers of LR-MSCs in those BAL samples were quantitated by measuring CFU-F. A significant correlation was noted between number of LR-MSCs and FOXF1 mRNA in the BAL (Pearson r=0.92; 95% CI=0.86 to 0.95; p<0.001). n=50 BAL samples Panel (C), FOXF1 expression in normal adult lungs. Expression of FOXF1 in normal human lung was assessed by in situ hybridization utilizing digoxigenin labeled RNA probe, followed by hematoxylin counterstaining. The area shown in bottom panels corresponds to the lesion marked by red frame in the top panel. The black arrowheads show cells positive for FOXF1. Magnification, ×100 top panel and ×600 bottom panel. Panel (D), FOXF1 expression in fibrotic lesions in human lung allografts. Representative sections of trans-bronchial lung biopsy demonstrating organizing pneumonia in a lung transplant recipient, stained for α-SMA (by immunohistochemical staining) and FOXF1 (by in situ hybridization). Left panel demonstrates a discrete area of organizing pneumonia with intense α-SMA staining signifying infiltration by myofibroblasts. FOXF1 mRNA expression was detected by in situ hybridization in the fibrotic area (center panel). Discrete spindle shaped cells demonstrating staining, consistent with FOXF1 expression, are noted in the area of organizing pneumonia. In situ hybridization utilizing DIG labeled control mRNA is shown on the right. Control for α-SMA staining is shown in FIG. 10. Magnification, ×400 Panel E, Co-expression of FOXF1 and α-SMA in fibrotic lesions. Section from human lung allograft biopsy demonstrating fibrotic lesions was examined for expression of FOXF1 and α-SMA using double-immunofluorescence microscopy. Rhodamine TSA and Fluorescein TSA was utilized to detect signal for FOXF1 and α-SMA respectively. Colocalization of FOXF1 and α-SMA in spindle shaped cells was noted demonstrating FOXF1 expression in myofibroblasts. Magnification, ×600 oil

FOXF1 expression in LR-MSCs was also compared to that in other lung resident cells such as endothelial and epithelial cells (FIG. 8A). Greater than 20,000 fold higher expression of FOXF1 was observed in LR-MSCs as compared to the human alveolar epithelial cells (A549) and primary bronchial epithelial cells, consistent with the fact that FOXF1 is specifically expressed only in the mesenchyme. Human pulmonary artery endothelial cells (HPAEC) demonstrated a 40-fold higher FOXF1 expression than epithelial cells, consistent with their embryonic mesenchyme derivation. However, the expression of FOXF1 in LRMSCs was noted to be 500-fold higher than that in endothelial cells. This uniquely high expression level of FOXF1 mRNA in LR-MSCs led prompted analysis of quantitative expression of FOXF1 transcript in the BAL fluid cell pellet as a marker of LR-MSC numbers. BAL from 50 lung transplant recipients was studied for both expression of FOXF1 mRNA and number of LR-MSCs. MSCs were quantitated by the number of colony forming units isolated from $2 \times 10^6$ plated BAL cells. A significant correlation was noted between the number of LR-MSCs in the BAL and FOXF1 mRNA (Pearson r=0.92; 95% CI=0.86 to 0.95; p<0.001) (FIG. 8B).

FOXF1 is Expressed in Myofibroblasts in Human Lung Transplant Biopsies

The markedly greater expression of FOXF1 in LR-MSCs than BM-MSCs also provided a tool to investigate whether myofibroblasts seen in the fibrotic lesions of lung allografts were derived from locally-resident lung-specific mesenchymal progenitor cells. Examination of the normal lung alveolar spaces demonstrated sparse FOXF1 expression, with cells demonstrating FOXF1 mRNA noted predominantly in the triangular corners of the alveoli or in the alveolar septa (FIG. 8C). Expression of FOXF1 mRNA and α-SMA protein was examined in biopsies demonstrating evidence of either BO or organizing pneumonia (n=5). Myofibroblasts, identified by their spindle shape and intensely positive α-SMA expression, were present in the fibrotic lesions. Robust expression of FOXF1 mRNA was noted in these lesions by in situ hybridization (FIG. 8D). To investigate the co-expression of FOXF1 and α-SMA, dual immunofluorescence staining was utilized. Co-localization of α-SMA and FOXF1 was noted in the spindle shaped cells present in the fibrotic lesions demonstrating that myofibroblasts in human lung allografts express FOXF1 (FIG. 8E). Since mesenchymal cells can also be potentially derived from local epithelium by epithelial-mesenchymal transformation (EMT), it was desirable to determine if this phenomenon when recapitulated in vitro is accompanied by expression of FOXF1. mRNA from A549 epithelial cells treated with TGF-β to induce EMT (Keshamouni et al. (2009) J. Proteome Res. 8:35-47; Willis et al. (2007) Am. J. Physiol. Lung Cell Mol. Physiol. 293:L525-534; Willis et al. (2005) 166:1321-1332; each incorporated by reference in its entirety) was analyzed by Affymetrix analysis. While EMT was associated with a loss of expression of the epithelial gene E-cadherin and an increase in expression of the mesenchymal genes N-cadherin, fibronectin-1, and vimentin, no induction of FOXF1 mRNA was noted (Table 6). Effect of TGF-β1 on FOXF1 expression in BM-MSCs, primary human bronchial cells and human endothelial cells (HPAECs) was also examined and no significant change was noted in the FOXF1 mRNA expression by real time PCR in the presence of this fibrogenic stimuli (P=0.45, 0.26 and 0.85 respectively)

TABLE 6

Gene expression in lung alveolar epithelial cells (A549) undergoing EMT in response to TGF-β (5 ng/ml).

| Gene Symbol | Name | Fold Change (from 0 Hours) | | | | | | | |
|---|---|---|---|---|---|---|---|---|---|
| | | 0.5 | 1 h | 2 h | 4 h | 8 h | 16 h | 24 h | 72 h |
| FOXF1 | Forkhead box F1 | 0.92 | 0.74 | 0.78 | 1.03 | 1.05 | 1.28 | 0.81 | 1.02 |
| CDH1 | E-cadherin | 1.00 | 1.03 | 0.99 | 0.56 | 0.66 | 0.23 | 0.14 | 0.10* |
| CDH2 | N-cadherin | 1.16 | 1.13 | 1.19 | 1.41 | 2.26 | 3.98 | 4.56 | 6.76* |
| FN1 | Fibronectin 1 | 1.03 | 1.02 | 0.92 | 1.15 | 1.31 | 1.91 | 2.91 | 5.14* |
| VIM | Vimentin | 1.89 | 2.18 | 2.62 | 2.57 | 2.90 | 2.89 | 3.19 | 4.24* |

*indicates P < 0.01 compared to 0 hours.

Discussion

Mesenchymal cell infiltration of the small airways, leading to fibrotic obliteration, is the primary feature of chronic lung allograft rejection or BO. Key pro-fibrotic mediators such as TGF-β and IL-13 have been linked to the pathogenesis of BO in both human samples and animal modeling (Lama et al. (2006) Am. J. Pathol. 169:47-60; Elssner et al. (2000) Transplantation 70:362-367; Ramirez et al. (2004) Am. J. Pathol. 165:1223-1232; Keane et al. (2007) J. Immunol. 178:511-519; each herein incorporated by reference in its entirety). However, the origin of the myofibroblasts critical for driving fibrogenesis in these injured lung allografts is less well understood. In this Experiment a MSC population demonstrated to be derived from the lung allograft itself was found to be unique in its high-level expression of lung embryonic mesenchymal-associated transcription factors. A markedly greater expression of transcription factors FOXF1 and specific HOX genes in LR-MSCs than BM-MSCs established the tissue specificity of solid organ-derived MSCs in humans. The ability of these tissue-specific mesenchymal progenitor cells to contribute to fibrogenesis was demonstrated by their capacity for in vitro myofibroblast differentiation in response to pro-fibrotic mediators, and their altered in vivo phenotype—marked by increased α-SMA expression and collagen secretion—in patients with BOS. Finally, FOXF1 expression in myofibroblasts in lung biopsies provided evidence for the local origin of these effector cells of fibrosis in lung transplants. These data, demonstrating the fibrotic differentiation potential of tissue-specific, organ-resident MSCs and the local mesenchymal origin of myofibroblasts in fibrotic lung allograft lesions, show a key role for local mesenchymal precursor cells in the fibrotic remodeling of a lung allograft.

By demonstrating the donor origin of multi-potent mesenchymal cells derived from human lung allografts, the tissue residence of connective tissue progenitor cells in solid organs was previously established (Lama et al. (2007) J. Clin. Invest. 117:989-996; herein incorporated by reference in its entirety). The data shown herein extend this observation by demonstrating that MSCs isolated from the lung allografts are not only resident but also tissue-specific progenitor cells, likely remnants of embryonic lung mesenchyme. LR-MSCs demonstrated high-level expression of mesenchymal transcription factors associated with developing lung mesenchyme. When compared to BM-MSCs, LR-MSCs expressed 35,000 fold more FOXF1, a mesenchymal transcription factor whose expression in splanchnic mesoderm is essential for lung development during embryogenesis (Cost et al. (2001) Am. J. Physiol. Lung Cell Mol. Physiol. 280:L823-838; Mahlapuu et al. (2001) Development 128:2397-2406; each herein incorporated by reference in its entirety). Similarly, the expression of HOX genes in LR-MSCs mirrors that noted during lung development, with a markedly greater expression of HOXA5 (Mahlapuu et al. (2001) Development 128:2397-2406; herein incorporated by reference in its entirety) and HOXB5 in LR-MSCs than BM-MSCs. Recent evidence indicates that mesenchymal cells in various adult tissues maintain key features of gene expression patterns established during embryogenesis (Chang et al. (2002) PNAS 99:12877-12882; herein incorporated by reference in its entirety). Similar expression of FOXF1 in MSCs from both BOS and non-BOS patients show that this same locally-derived population is found in both states of quiescence/organized repair as well as fibrosis.

It was demonstrated that lung allograft-derived MSCs can differentiate into a fibrogenic phenotype by exposure to components of the pro-fibrotic milieu known to be present in BOS. The effect of two important mediators, TGF-β and IL-13, on LR-MSC fibrotic differentiation was examined. Both TGF-β and IL-13 have been strongly linked to pathogenesis of BO in animal models of tracheal transplantation and have also been shown to be increased in BAL fluid from patients with BOS (Lama et al. (2006) Am. J. Pathol. 169:47-601 Elssner et al. (2000) Transplantation 70:362-367; Ramirez et al. (2004) Am J. Pathol. 165:1223-1232; Keane et al. (2007) J. Immunol. 178:511-519; each herein incorporated by reference in its entirety). LR-MSCs demonstrated myofibroblast differentiation, marked by both an increased collagen I synthetic ability and α-SMA expression, in response to TGF-β and IL-13. More significantly, mesenchymal cells from BAL of patients with BOS demonstrated a stable increase in the α-SMA and collagen expression, showing that cellular phenotype is skewed towards that of a differentiated myofibroblast during the development of disease. High FOXF1 expression, noted in the cells obtained from patients with BOS, demonstrates their graft/donor derivation. This is also supported by study of cytogenetic analyses in sex-mismatched lung transplant recipients, where 98% of the cells from patients with BOS were donor in origin (Lama et al. (2007) J. Clin. Invest. 117:989-996; herein incorporated by reference in its entirety). An increase in LR-MSCs in BAL precedes the development of BOS, further reiterating a potential role of these local-mesenchymal cells in BOS pathogenesis (Experiment 1).

While the present invention is not limited to any particular mechanism, and an understanding of the mechanism is not necessary to practice the present invention, it is contemplated that the ability of LR-MSCs to undergo fibrotic differentiation in response to soluble mediators present in an allograft micro-environment during BOS development, and the stable fibrotic phenotypic alterations in LR-MSCs in BOS patients point to a possible pathogenic role for endogenous MSCs as effector cells in the pathogenesis of BOS. This notion of MSCs as a driver of fibrosis appears contradictory to recent literature ascribing an immunoregulatory/anti-fibrotic role to this cell, however such studies primarily employed models of acute injury (Gupta et al. (2007) J. Immunol. 179:1855-1863; Ortiz et al. (2003) PNAS 100:8407-8411; Rojas et al. (2005) Am. J. Respir. Cell Mol. Biol. 33:145-152; each herein incorporated by reference in its entirety). In chronic injury models, a condition more relevant to BOS, exogenous MSCs have been reported to contribute to fibrosis (di Bonzo et al. (2008) Gut 57:225-231; Wu et al. (2005) J. Heart Lung Transplant 24:2160-2169; each herein incorporated by reference in its entirety). MSCs including LR-MSCs demonstrate an in vitro potential to inhibit T cell function via secretion of soluble mediators such as prostaglandin E2 (Jarvinen et al. (2008) J. Immunol. 181:4389-4396; Aggarwal et al. (2005) Blood 105: 1815-1822; each herein incorporated by reference in its entirety). However, it has also been demonstrated that MSCs potentiate fibrotic differentiation of other mesenchymal cells by secreting pro-fibrotic mediators such as TGF-ß1 (Salazar et al. (2009) Am. J. Physiol. Lung Cell Mol. Physiol. 297: L1002-1011; herein incorporated by reference in its entirety). Thus, while the present invention is not limited to any particular mechanism, and an understanding of the mechanism is not necessary to practice the present invention, it is contemplated that while MSCs can modulate an inflammatory microenvironment, they can also promote fibrogenesis by secreting pro-fibrotic mediators (Salazar et al. (2009) Am. J. Physiol. Lung Cell Mol. Physiol. 297:L1002-1011; herein incorporated by reference in its entirety) or differentiating to myofibroblasts. Regulation of native LR-MSC synthetic function and fibrotic differentiation fate by the local milieu plays a central role in dictating whether these cells serve a predominant immunoregulatory function or instead promote fibroproliferative events which favor the development of BO.

Myofibroblasts in solid organs can be potentially derived from diverse cellular pools (Hinz et al. (2007) Am. J. Pathol. 170:1807-1816; herein incorporated by reference in its entirety). Bone marrow, home to mesenchymal precursors such as $CD45^+Col\ I^+$ fibrocytes (Bucala et al. (1994) Mol. Med. 1:71-81; herein incorporated by reference in its entirety) and $CD45^-Col\ I^+MSCs$ (Pittenger et al. (1999) Science 284:143-147; herein incorporated by reference in its entirety), is a distant reservoir of mesenchymal precursor cells. Organ resident sources include a local pool of mesenchymal progenitor cells or a somatic cell capable of trans-differentiation such as seen in EMT (Iwano et al. (2002) J. Clin. Invest. 110:341-350; herein incorporated by reference in its entirety). Biological/signaling mechanisms involved in recruitment/differentiation depend on the compartment from which the participating precursor cells are derived; hence it is important to distinguish the relative contribution of each compartment in specific diseases. However, the lack of unique markers of mesenchymal progenitor cells from various sources makes the human investigation of this question difficult. In experiments detailed herein, FOXF1 was identified as a transcription factor uniquely expressed in lung-derived as compared to bone marrow-derived MSCs. FOXF1 expression in α-SMA expressing cells in fibrotic lesions provides a human demonstration of the local origin of myofibroblasts. These data demonstrating a lung rather than a bone marrow origin of myofibroblasts thus support the studies of bone marrow chimeric animals, where in spite of evidence of recruitment of bone marrow derived fibroblasts to remodeling lung, myofibroblasts present in the fibrotic lesions were not derived from bone marrow progenitors (Dolgachev et al. (2009) Am. J. Pathol. 174:390-400; Hashimoto et al. (2004) J. Clin. Invest. 113:243-252; each herein incorporated by reference in its entirety). These human studies also complement animal studies of gene-labeled mice demonstrating local tissue resident mesenchymal rather than epithelial cells as precursors of collagen secreting myofibroblasts in the kidney (Humphrys et al. (2010) Am. J. Pathol. 176:85-97; herein incorporated by reference in its entirety). The fibrotic cells in these kidney injury models arose from resident cells expressing FoxD1, the forkhead transcription factor seen in embryonic mesenchyme fated to become stromal cells of the kidney (Humphrys et al. (2010) Am. J. Pathol. 176:85-97; herein incorporated by reference in its entirety).

Experiments described herein establish the tissue specificity and local origin of MSCs isolated from human lungs. While the present invention is not limited to any particular mechanism, and an understanding of the mechanism is not necessary to practice the present invention, it is contemplated that the ability of these easily obtainable graft-resident mesenchymal precursor cells to undergo fibrotic differentiation and their altered profibrotic phenotype in BOS not only indicates a role for these cells in the pathogenesis of this disorder, but also demonstrates an opportunity to utilize them as a sentinel cell biomarker of fibroproliferation. Furthermore, the unique expression of FOXF1 in human lung allograft-derived MSCs, the observed failure of up-regulation of FOXF1 in in vitro EMT studies, and FOXF1 expression in myofibroblasts in human tissues in situ provides evidence that local mesenchymal progenitors in humans, likely remnants of the embryonic tissue mesenchyme, are the predominant source of myofibroblasts in lung fibrogenesis post-transplantation.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in organ transplant, molecular biology, immunology or related fields are intended to be within the scope of the following claims.

I claim:

1. A method of assessing the risk of bronchiolitis obliterans syndrome in a post lung transplant subject, comprising:
   a) obtaining a sample of bronchoalveolar lavage fluid from a post lung transplant subject;
   b) quantitating the number of lung-resident mesenchymal stem cells in said sample bronchoalveolar lavage fluid; wherein said quantitating comprises isolating nucleated cells from said sample and culturing said isolated cells to generate single separated fibroblastoid colonies and
   c) determining an increased risk of bronchiolitis obliterans syndrome in said subject when a level of single separated fibroblast colonies of at least 10 colonies per $2 \times 10^6$ of isolated nucleated cells is present in said sample bronchoalveolar lavage fluid.

2. The method of claim 1, wherein said subject is human.

3. The method of claim 1, wherein said post lung transplant subject received a transplanted lung at least 3 month prior to the obtaining of said sample of bronchoalveolar lavage fluid.

* * * * *